United States Patent
Xu et al.

(10) Patent No.: US 10,702,858 B2
(45) Date of Patent: Jul. 7, 2020

(54) METHODS OF HYDROFLUORINATION

(71) Applicant: UNIVERSITY OF LOUISVILLE RESEARCH FOUNDATION, INC., Louisville, KY (US)

(72) Inventors: Bo Xu, Louisville, KY (US); Zhichao Lu, Louisville, KY (US); Gerald B. Hammond, Shelbyville, KY (US)

(73) Assignee: UNIVERSITY OF LOUISVILLE RESEARCH FOUNDATION, INC., Louisville, KY (US)

( * ) Notice: Subject to any disclaimer, the term of this patent is extended or adjusted under 35 U.S.C. 154(b) by 0 days.

(21) Appl. No.: 16/214,793

(22) Filed: Dec. 10, 2018

(65) Prior Publication Data

US 2019/0176134 A1 Jun. 13, 2019

Related U.S. Application Data

(60) Provisional application No. 62/596,937, filed on Dec. 11, 2017.

(51) Int. Cl.
| | | |
|---|---|---|
| *B01J 27/055* | (2006.01) | |
| *C07D 277/56* | (2006.01) | |
| *C07C 67/287* | (2006.01) | |
| *C07C 303/30* | (2006.01) | |
| *C07D 209/50* | (2006.01) | |
| *C07C 303/34* | (2006.01) | |
| *C07C 201/12* | (2006.01) | |
| *C07C 213/08* | (2006.01) | |
| *C07C 253/30* | (2006.01) | |
| *C07C 45/63* | (2006.01) | |
| *C07D 215/227* | (2006.01) | |
| *C07D 307/68* | (2006.01) | |
| *C07D 333/38* | (2006.01) | |
| *C07D 207/34* | (2006.01) | |
| *C01D 5/00* | (2006.01) | |
| *C07C 17/087* | (2006.01) | |
| *C07C 67/307* | (2006.01) | |
| *C07C 51/363* | (2006.01) | |
| *C07B 39/00* | (2006.01) | |
| *C07C 29/62* | (2006.01) | |
| *B01J 31/00* | (2006.01) | |

(52) U.S. Cl.
CPC ............ *B01J 27/055* (2013.01); *B01J 31/00* (2013.01); *C01D 5/00* (2013.01); *C07B 39/00* (2013.01); *C07C 17/087* (2013.01); *C07C 29/62* (2013.01); *C07C 45/63* (2013.01); *C07C 51/363* (2013.01); *C07C 67/287* (2013.01); *C07C 67/307* (2013.01); *C07C 201/12* (2013.01); *C07C 213/08* (2013.01); *C07C 253/30* (2013.01); *C07C 303/30* (2013.01); *C07C 303/34* (2013.01); *C07D 207/34* (2013.01); *C07D 209/50* (2013.01); *C07D 215/227* (2013.01); *C07D 277/56* (2013.01); *C07D 307/68* (2013.01); *C07D 333/38* (2013.01); *C07C 2601/02* (2017.05); *C07C 2601/14* (2017.05); *C07C 2601/16* (2017.05); *C07C 2602/28* (2017.05)

(58) Field of Classification Search
CPC ............... C07D 207/34; C07D 209/50; C07D 215/227; C07D 277/56; C07D 307/68; C07D 333/38; C07C 17/087; C07C 29/62; C07C 45/63; C07C 51/363; C07C 67/287; C07C 67/307; C07C 201/12; C07C 213/08; C07C 253/30; C07C 303/30; C07C 303/34; C07C 2601/02; C07C 2601/16; C07C 2601/14; C07C 2602/28; C07B 39/00; C01D 5/00; B01J 27/055; B01J 27/12; B01J 31/00
USPC ................................................. 502/217, 224
See application file for complete search history.

(56) References Cited

U.S. PATENT DOCUMENTS

| | | | | | |
|---|---|---|---|---|---|
| 2,430,181 | A | * | 11/1947 | Linn | C07C 2/62 585/724 |
| 2,716,143 | A | * | 8/1955 | Skiles | C07C 17/08 570/154 |
| 3,200,159 | A | * | 8/1965 | Sedlak | C07C 17/00 570/145 |
| 3,555,102 | A | * | 1/1971 | Ogura | B01J 27/00 570/154 |
| 3,646,230 | A | * | 2/1972 | Kung | C07C 17/08 570/154 |
| 3,778,500 | A | * | 12/1973 | Briggs | C01G 43/00 423/253 |

OTHER PUBLICATIONS

Abraham (1993) "Scales of solute hydrogen-bonding: their construction and application to physicochemical and biochemical processes" Chem. Soc. Rev., vol. 22, pp. 73-83.
Abraham et al., (1989) "Hydrogen bonding. Part 7. A scale of solute hydrogen-bond acidity based on log K values for complexation in tetrachloromethane" J. Chem. Soc., Perkin Trans. 2, pp. 699-711.
Abraham et al., (1990) "Hydrogen bonding. Part 10. A scale of solute hydrogen-bond basicity using log K values for complexation in tetrachloromethane" J. Chem. Soc., Perkin Trans. 2, pp. 521-529.
Abraham et al., (2001) "Hydrogen Bond Structural Group Constants" J. Org. Chem., vol. 66, pp. 3484-3491.
Abraham et al., (2004) "Determination of Solvation Descriptors for Ionic Species: Hydrogen Bond Acidity and Basicity" J. Org. Chem., vol. 69, pp. 4677-4685.

(Continued)

*Primary Examiner* — Patricia L. Hailey
(74) *Attorney, Agent, or Firm* — ALGM LLP; Harry J. Guttman

(57) ABSTRACT

Some embodiments of the invention include inventive catalysts (e.g., compounds of Formula (I) or (Ia)). Other embodiments include compositions comprising the inventive catalysts. Some embodiments include methods of using the inventive catalysts (e.g., in hydrofluorination of an organic compound). Further embodiments include methods for making the inventive catalysts. Additional embodiments of the invention are also discussed herein.

25 Claims, 3 Drawing Sheets
(3 of 3 Drawing Sheet(s) Filed in Color)

(56) References Cited

OTHER PUBLICATIONS

Ashtekar et al., (2016) "Nucleophile-Assisted Alkene Activation: Olefins Alone Are Often Incompetent" J. Am. Chem. Soc., vol. 138, pp. 8114-8119.
Barker et al., (2012) "Fe(III)/NaBH4-Mediated Free Radical Hydrofluorination of Unactivated Alkenes" J. Am. Chem. Soc., vol. 134, pp. 13588-13591.
Bucsi et al., (2002) "Stable Dialkyl Ether/Poly(Hydrogen Fluoride) Complexes: Dimethyl Ether/Poly(Hydrogen Fluoride), A New, Convenient, and Effective Fluorinating Agent1a" J. Am. Chem. Soc., vol. 124, pp. 7728-7736.
Carey et al., Advanced Organic Chemistry, Part A: Structure and Mechanisms, 5th edition, vol. A. (2007) Chapter 5 Springer, Boston, MA.
Champagne et al., (2015) "Monofluorination of Organic Compounds: 10 Years of Innovation" Chem. Rev., vol. 115, pp. 9073-9174.
Chan et al., (2011) "Palladium(II)-Catalyzed Selective Monofluorination of Benzoic Acids Using a Practical Auxiliary: A Weak-Coordination Approach" Angew. Chem. Int. Ed., vol. 50, pp. 9081-9084.
Emer et al., (2014) "cis-Specific Hydrofluorination of Alkenylarenes under Palladium Catalysis through an Ionic Pathway" Angew. Chem. Int. Ed., vol. 53, pp. 4181-4185.
Fier et al., (2012) "Copper-Mediated Fluorination of Aryl Iodides" J. Am. Chem. Soc., vol. 134, pp. 10795-10798.
Furuya et al., (2011) "Catalysis for fluorination and trifluoromethylation" Nature, vol. 473, pp. 470-477.
Grushin (2010) "The Organometallic Fluorine Chemistry of Palladium and Rhodium: Studies toward Aromatic Fluorination" Acc. Chem. Res., vol. 43, pp. 160-171.
Haufe (1996) "Triethylamine Trishydrofluoride in Synthesis" J. Prakt. Chem. /Chem-Ztg, vol. 338, pp. 99-113.
Katcher et al., (2010) "Palladium-Catalyzed Asymmetric Synthesis of Allylic Fluorides" J. Am. Chem. Soc., vol. 132, pp. 17402-17404.
Laurence et al., (2009) "The pKBHX Database: Toward a Better Understanding of Hydrogen-Bond Basicity for Medicinal Chemists" J. Med. Chem., vol. 52, pp. 4073-4086.
Liang et al., (2017) "Hydrogen Bonding: Regulator for Nucleophilic Fluorination" Chem. Eur. J., vol. 23, No. 71, pp. 17850-17861.
Muller et al., (2007) "Fluorine in pharmaceuticals: Looking beyond intuition" Science, vol. 317, pp. 1881-1886.
Okoromoba et al., (2014) "Designer HF-Based Fluorination Reagent: Highly Regioselective Synthesis of Fluoroalkenes and gem-Difluoromethylene Compounds from Alkynes" J. Am. Chem. Soc., vol. 136, pp. 14381-14384.
Okoromoba et al., (2015) "Preparation of Fluorinated Tetrahydropyrans and Piperidines using a New Nucleophilic Fluorination Reagent DMPU/HF" Org. Lett., vol. 17, pp. 3975-3977.
Okoromoba et al., (2016) "Achieving regio- and stereo-control in the fluorination of aziridines under acidic conditions" Chem. Commun., vol. 52, pp. 13353-13356.
Olah et al., (1973) "Synthetic Methods and Reactions II1. Hydrofluorination of Alkenes, Cyclopropane and Alkynes with Poly-Hydrogen Fluoride/Pyridine (Trialkylamine)Reagents" Synthesis, vol. 1973, No. 12, pp. 779-780.
Olah et al., (1978) "Fluorinations with pyridinium polyhydrogen fluoride reagent: 1-fluoroadamantane. (Tricyclo [3.3.1.13,7]decane, 1-fluoro-)" Org. Synth., vol. 58, pp. 75-79.
Olah et al., (1979) "Synthetic methods and reactions. 63. Pyridinium poly(hydrogen fluoride) (30% pyridine-70% hydrogen fluoride): a convenient reagent for organic fluorination reactions" J. Org. Chem., vol. 44, pp. 3872-3881.
Pike et al., (2017) "H-Bond Acceptor Parameters for Anions" J. Am. Chem. Soc., vol. 139, pp. 6700-6706.
Schevenels et al., (2017) "Isolable and Readily Handled Halophosphonium Pre-reagents for Hydro- and Deuteriohalogenation" J. Am. Chem. Soc., vol. 139, pp. 6329-6337.
Shigehisa et al., (2013) "Cobalt-Catalyzed Hydrofluorination of Unactivated Olefins: A Radical Approach of Fluorine Transfer" Org. Lett., vol. 15, pp. 5158-5161.
Smith et al., (2015) "The Contrasting Character of Early and Late Transition Metal Fluorides as Hydrogen Bond Acceptors" J. Am. Chem. Soc., vol. 137, pp. 11820-11831.
Thibaudeau et al., (2007) "A novel, facile route to [small beta]-fluoroamines by hydrofluorination using superacidHF-SbF5" Chem. Commun., pp. 3198-3200.
Xu et al., (2017) "Hypervalent Iodine(III)-Mediated Oxidative Fluorination of Alkylsilanes by Fluoride Ions" Angew. Chem. Int. Ed., vol. 56, pp. 1101-1104.
Yoneda (1991) "The combination of hydrogen fluoride with organic bases as fluorination agents" Tetrahedron, vol. 47, pp. 5329-5365.

* cited by examiner

HOMO of 1p

METHODS OF HYDROFLUORINATION

CROSS-REFERENCE TO RELATED APPLICATIONS

This application claims the benefit of U.S. Provisional Application No. 62/596,937, filed Dec. 11, 2017, entitled "METHODS OF HYDROFLUORINATION", which is herein incorporated by reference in its entirety.

GOVERNMENT RIGHTS

This invention was made with government support under 1R01GM121660 awarded by the National Institutes of Health. The government has certain rights in the invention.

BACKGROUND

The growing applications of fluorine in pharmaceuticals, agrochemicals, and materials has stimulated interest in fluorination methodologies. Because alkenes can sometimes be important functionalities, finding a broadly applicable alkene hydrofluorination protocol can help in the preparation of fluorinated compounds. Several hydrofluorination protocols have been developed, but they have several deficiencies, such as, one or more of: limited to certain alkenes, harsh reaction conditions, use of environmentally undesirable atoms or compounds, required reductants, required expensive electrophilic fluorination reagents, required metal catalysts, use of strong reductants, or use of strong oxidants.

Certain embodiments of the invention address one or more of the deficiencies described above. Some embodiments of the invention include inventive catalysts (e.g., compounds of Formula (I) or (Ia)). Other embodiments include compositions comprising the inventive catalysts. Some embodiments include methods of using the inventive catalysts (e.g., in hydrofluorination of an organic compound). Further embodiments include methods for making the inventive catalysts. Additional embodiments of the invention are also discussed herein.

SUMMARY

Some embodiments of the present invention include a catalyst selected from (a) MHSO$_4$-xHF (Ia), (b) M$_2$SO$_4$-xHF (Ib), and (c) M$^a$SO$_4$-xHF (Ic) (collectively Formula (Ia), Formula (Ib), and Formula (Ic) are referred to as Formula (I)), where M is Li$^+$, Na$^+$, K$^+$, Rb$^+$, Cs$^+$, or NH$_4^+$, M$^a$ is Be$^{2+}$, Mg$^{2+}$, Ca$^{2+}$, Sr$^{2+}$, Ba$^{2+}$, Fe$^{2+}$, Zn$^{2+}$, Mn$^{2+}$, Ni$^{2+}$, Co$^{2+}$, or Cu$^{2+}$, and x is 1, 2, 3, 4, 5, 6, 7, 8, 9, 10, 11, 12, 13, 14, 15, or 16. Other embodiments include a composition comprising the catalyst (e.g., as described herein) and a solvent. In certain embodiments, the solvent can be DCM (dichloromethane), DCE (1,2 dichloroethane), dioxane, Et$_2$O (diethylether), CH$_3$CN, EtOAc (ethyl acetate), DMSO (dimethyl sulfoxide), DMF (dimethyl formamide), or toluene.

Other embodiments of the present invention include a method for hydrofluorination of an organic compound comprising one or more alkenes, where the method comprises contacting an organic compound comprising one or more alkenes with a catalyst of Formula (I) wherein the contacting is optionally in the presence of a solvent. In some embodiments, the method comprises (a) providing a mixture of a solvent and the organic compound comprising one or more alkenes; and (b) contacting the composition of (a) with a catalyst of Formula (I) to provide a product molecule. In still other embodiments, the product molecule comprises one F on one of the carbons where an alkene was in the organic compound comprising one or more alkenes.

Some embodiments of the present invention include a method for preparing the catalyst.

Other embodiments of the invention are also discussed herein.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

The following drawings form part of the present specification and are included to further demonstrate certain aspects of the present invention. The invention may be better understood by reference to one or more of these drawings in combination with the description of specific embodiments presented herein.

DETAILED DESCRIPTION

Figure 1:
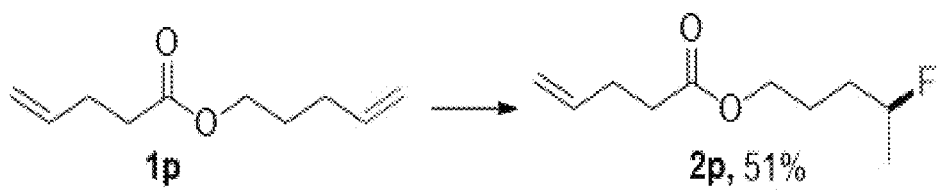
FIG. 1: Calculated HOMO (Highest Occupied Molecular Orbital) for diene 1p is shown.
Figure 1:
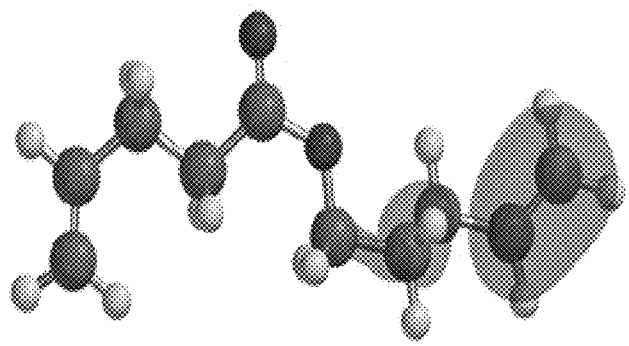

While embodiments encompassing the general inventive concepts may take diverse forms, various embodiments will be described herein, with the understanding that the present disclosure is to be considered merely exemplary, and the general inventive concepts are not intended to be limited to the disclosed embodiments.

Some embodiments of the invention include inventive catalysts (e.g., compounds of Formula (I) or (Ia)). Other embodiments include compositions comprising the inventive catalysts. Some embodiments include methods of using the inventive catalysts (e.g., in hydrofluorination of an organic compound). Further embodiments include methods for making the inventive catalysts. Additional embodiments of the invention are also discussed herein.

Some embodiments of the invention include catalysts (e.g., hydrofluorination catalysts) of Formulas (Ia), (Ib), and (Ic) (collectively Formula (Ia), Formula (Ib), and Formula (Ic) are referred to as Formula (I)):

MHSO$_4$-xHF        (Ia),

M$_2$SO$_4$-xHF        (Ib), or

M$^a$SO$_4$-xHF        (Ic).

In some embodiments, M can be Li$^+$, Na$^+$, K$^+$, Rb$^+$, Cs$^+$, or NH$_4^+$. In certain embodiments, M can be Na$^+$, K$^+$, or NH$_4^+$ (e.g., with Formula (Ia)). In yet other embodiments, M can be K$^+$ (e.g., with Formula (Ia)). In still other embodiments, M$^a$ can be Be$^{2+}$, Mg$^{2+}$, Ca$^{2+}$, Sr$^{2+}$, Ba$^{2+}$, Fe$^{2+}$, Zn$^{2+}$, Mn$^{2+}$, Ni$^{2+}$, Co$^{2+}$, or Cu$^{2+}$. In other embodiments, x can be 1, 2, 3, 4, 5, 6, 7, 8, 9, 10, 11, 12, 13, 14, 15, or 16. In other embodiments, x can be 6, 7, 8, 9, 10, 11, 12, 13, 14, 15, or 16. In some embodiments, x can be 8, 9, 10, 11, 12, 13, or 14 (e.g., with Formula (Ia)). In other embodiments, x can be 13 (e.g., with Formula (Ia)).

In some embodiments, the MHSO$_4$, the M$_2$SO$_4$, or the M$^a$SO$_4$ have a hydrogen bond basicity ($\beta$) of about 7, about 8, about 9, about 10, about 11, about 12, about 13, about 14, about 15, or about 16. In other embodiments, the $MHSO_4$, the $M_2SO_4$, or the $M^aSO_4$ have a hydrogen bond basicity ($\beta$) of about 10, about 11, about 12, or about 13. In yet other embodiments, the $MHSO_4$, the $M_2SO_4$, or the $M^aSO_4$ have a pKa of about 0.5, about 0.6, about 0.7, about 0.8, about 0.9, about 1.0, about 1.1, about 1.2, about 1.3, about 1.4, about 1.5, about 1.6, about 1.7, about 1.8, about 1.9, about 2.0, about 2.1, about 2.2, about 2.3, about 2.4, or about 2.5. In some embodiments, the $MHSO_4$, the $M_2SO_4$, or the $M^aSO_4$ have a pKa of about 1.4, about 1.5, about 1.6, about 1.7, about 1.8, about 1.9, about 2.0, about 2.1, about 2.2, or about 2.3.

Some embodiments of the invention include methods for making catalysts of Formula (I) comprising contacting HF with $MHSO_4$, $M_2SO_4$, or $M^aSO_4$. The contacting can be any suitable form of contacting including but not limited to contacting solid $MHSO_4$, $M_2SO_4$, or $M^aSO_4$ with gaseous HF. In other embodiments, $MHSO_4$, $M_2SO_4$, or $M^aSO_4$ (e.g., in solid form) is added to a Teflon tube and HF gas is added to the Teflon tube (e.g., with stirring or with shaking). In still other embodiments, the Teflon tube (e.g., prior to adding the HF) can be cooled to any suitable temperature including but not limited to about −20° C., about −10° C., about −5° C., about 0° C., about 5° C., or about 10° C. In yet other embodiments, the Teflon tube during the addition and/or after the addition can be at any suitable temperature (e.g., maintained at a temperature) including but not limited to about −20° C., about −10° C., about −5° C., about 0° C., about 5° C., about 10° C., about 15° C., about 20° C., about 25° C., at least about −20° C., at least about −10° C., at least about 0° C., no more than about 20° C., no more than about 10° C., no more than about 5° C., or no more than about 0° C. In certain embodiments, the mole ratio of added HF to added $MHSO_4$, $M_2SO_4$, or $M^aSO_4$ can be any suitable mole ratio including but not limited to about 0.1, about 0.5, about 1, about 2, about 3, about 4, about 5, about 6, about 7, about 8, about 9, about 10, about 11, about 12, about 13, about 14, about 15, about 16, about 17, about 18, about 19, about 20, about 21, about 22, about 23, about 24, about 25, at least about 0.1, at least about 1, at least about 5, at least about 10, at least about 15, at least about 20, no more than about 20, or no more than about 25. In some embodiments, the product can be stable at room temperature (e.g., about 23° C.) or can be stable at about 4° C.

Some embodiments of the invention include compositions comprising catalysts (e.g., hydrofluorination catalysts) of Formulas (Ia), (Ib), and (Ic) (collectively Formula (Ia), Formula (Ib), and Formula (Ic) are referred to as Formula (I)). In certain embodiments, the compositions comprise catalysts of Formula (I) and a solvent. In other embodiments, the solvent is any suitable solvent (e.g., for performing hydrofluorination) including but not limited to DCM (dichloromethane), DCE (1,2 dichloroethane), dioxane, $Et_2O$ (diethylether), $CH_3CN$, EtOAc (ethyl acetate), DMSO (dimethyl sulfoxide), DMF (dimethyl formamide), or toluene. In still other embodiments, the solvent is DCM, DCE, or toluene. In yet other embodiments, the solvent is a weak hydrogen bond acceptor. In some embodiments, the composition further comprises an organic compound comprising one or more alkenes.

Some embodiments of the present invention include methods for hydrofluorination of an organic compound comprising one or more alkenes. The hydrofluorination product can be an altered reactant organic compound comprising one or more alkenes which as a result of hydrofluorination has one or more additional fluorines at carbons which previously were part of the one or more alkenes in the reactant organic compound.

In other embodiments of the methods for hydrofluorination, the organic compound comprising one or more alkenes can comprise any suitable alkene including but not limited to alkenes that are:

(a) monosubstituted alkenes (e.g.,

to provide

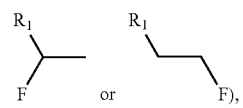

(b) disubstituted alkenes (e.g.,

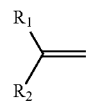

to provide

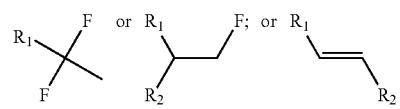

to provide

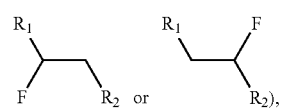

or (c) trisubstituted alkenes (e.g.,

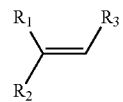

to provide

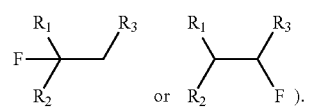

Figure 2:
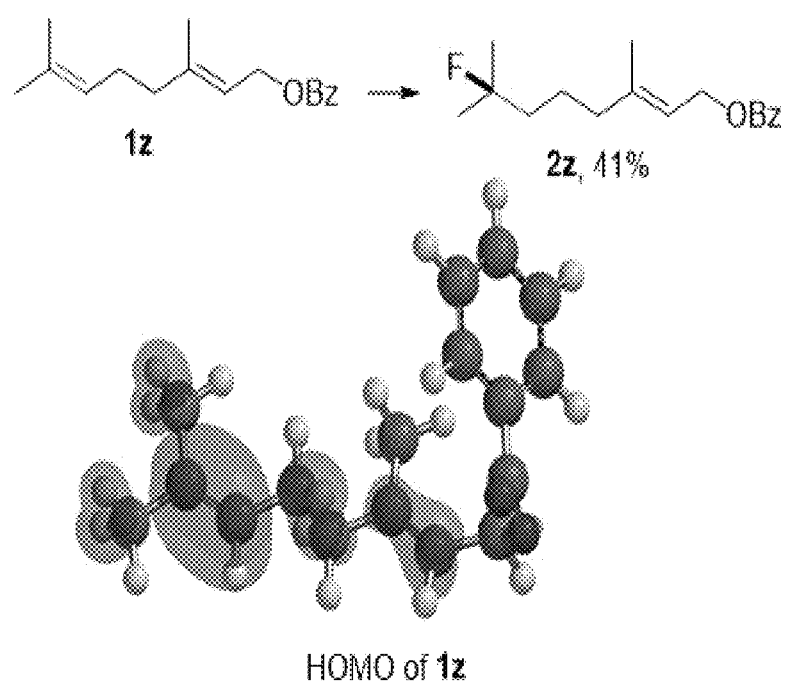
FIG. 2: Calculated HOMO (Highest Occupied Molecular Orbital) for diene 1z is shown.
Figure 3:
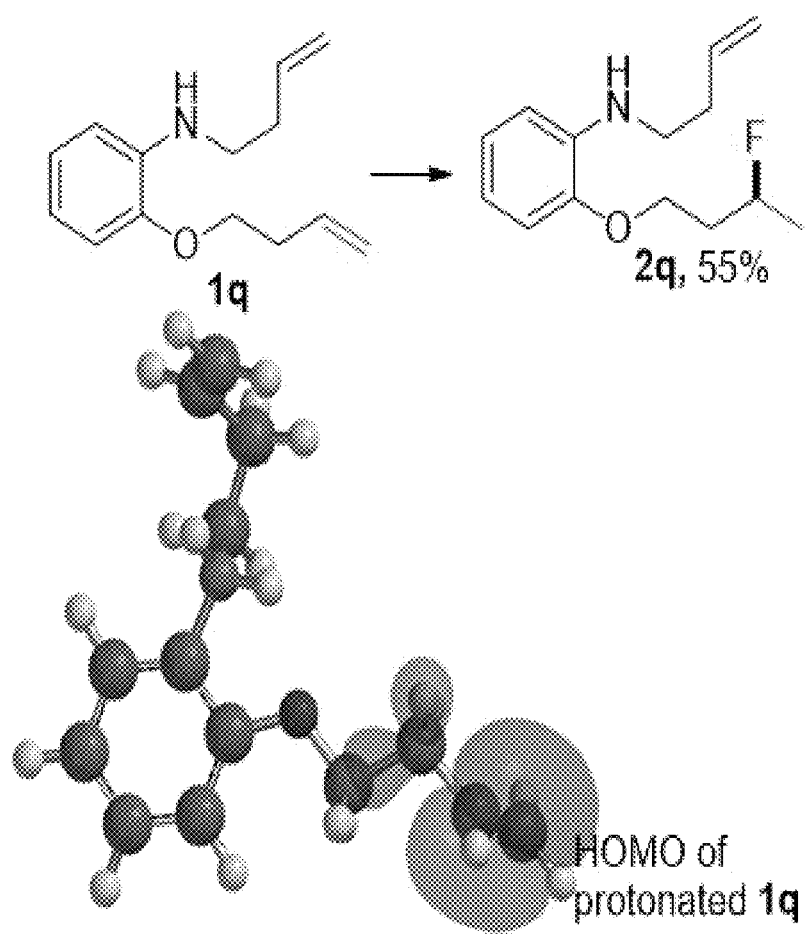
FIG. 3: Calculated HOMO (Highest Occupied Molecular Orbital) for diene 1q is shown.

In some embodiments, $R_1$, $R_2$, and $R_3$ can comprise or be any suitable moiety, such as but not limited to those provided in Table 2 (a-d), FIGS. 1-3, and the Examples. In other embodiments, one or more of $R_1$, $R_2$, or $R_3$ can comprise one or more of any moiety such as but not limited to one or more of ester, sulfonate, amide, ether, nitro, nitrile, aldehyde, amine, heterocycle, quinoline, furan, thiophene, pyrrole thiazole, alcohol, primary alcohol, secondary alcohol, tertiary alcohol, α, β unsaturated ketone, carboxylic acid, halogen, aryl, benzyl, phenyl, heteroaryl, alkyl, alkenyl, alkynyl, alkoxy, —CN, sulfo, morpholinyl, —$CONH_2$, —$CON(CH_3)_2$, $C_1$-$C_3$ perfluoronated alkyl, —$CF_3$, —$OCF_3$, or cyclic alkyl (e.g., cyclopropyl). In some embodiments, one or more of $R_1$, $R_2$, or $R_3$ can be a short alkyl (e.g., $C_1$, $C_2$, $C_3$, $C_4$, $C_5$, $C_6$, or $C_7$ alkyl). In certain embodiments, fluorination can occur at the alkene carbon that has more substitutions (e.g., as per Markovnikov's rule). In other embodiments, if there is more than one alkene, the hydrofluorination can occur at the alkene that is more electron rich (e.g., having a higher HOMO orbital energy and/or density). In some embodiments, the organic compound comprising one or more alkenes can have any suitable molecular weight including but not limited to about 28 daltons, about 100 daltons, about 200 daltons, about 300 daltons, about 400 daltons, about 500 daltons, about 600 daltons, about 700 daltons, about 800 daltons, about 900 daltons, about 1,000 daltons, about 5,000 daltons, about 10,000 daltons, about 20,000 daltons, about 30,000 daltons, about 40,000 daltons, about 50,000 daltons, about 75,000 daltons, about 100,000 daltons, about 250,000 daltons, about 1,000,000 daltons, at least about 28 daltons, at least about 100 daltons, at least about 200 daltons, no more than about 100 daltons, no more than about 1,000 daltons, no more than about 5,000 daltons, no more than about 10,000 daltons, no more than about 50,000 daltons, no more than about 100,000 daltons, no more than about 500,000 daltons, or no more than about 1,000,000 daltons.

In some embodiments, methods for hydrofluorination can comprise contacting the organic compound comprising one or more alkenes with a catalyst of Formula (I) (e.g., Formula (Ia) or Formula (Ib)) to provide a product molecule. In certain embodiments, the contacting is in the presence of a solvent (e.g., with the organic compound, with the catalyst, or both). In other embodiments, methods for hydrofluorination can comprise (a) providing a mixture of a solvent and the organic compound comprising one or more alkenes (e.g., adding solvent to the catalyst or adding catalyst to the solvent), and then (b) contacting the composition of (a) with a catalyst of Formula (I) (e.g., Formula (Ia) or Formula (Ib)) to provide a product molecule.

In other embodiments of the methods for hydrofluorination, M can be $Li^+$, $Na^+$, $K^+$, $Rb^+$, $Cs^+$, or $NH_4^+$. In certain embodiments, M can be $Na^+$, $K^+$, or $NH_4^+$ (e.g., with Formula (Ia)). In yet other embodiments, M can be $K^+$ (e.g., with Formula (Ia)). In some embodiments, $M^a$ can be $Be^{2+}$, $Mg^{2+}$, $Ca^{2+}$, $Sr^{2+}$, $Ba^{2+}$, $Fe^{2+}$, $Zn^{2+}$, $Mn^{2+}$, $Ni^{2+}$, $Co^{2+}$, or $Cu^{2+}$. In certain embodiments, $M^a$ can be $Be^{2+}$, $Mg^{2+}$, $Ca^{2+}$, $Sr^{2+}$, $Ba^{2+}$, $Fe^{2+}$, $Zn^{2+}$, $Mn^{2+}$, $Ni^{2+}$, $Co^{2+}$, or $Cu^{2+}$. In other embodiments, x can be 1, 2, 3, 4, 5, 6, 7, 8, 9, 10, 11, 12, 13, 14, 15, or 16. In still other embodiments, x can be 6, 7, 8, 9, 10, 11, 12, 13, 14, 15, or 16. In some embodiments, x can be 8, 9, 10, 11, 12, 13, or 14 (e.g., with Formula (Ia)). In other embodiments, x can be 13 (e.g., with Formula (Ia)).

In other embodiments of the methods for hydrofluorination, the solvent is any suitable solvent (e.g., for performing hydrofluorination) including but not limited to DCM (dichloromethane), DCE (1,2 dichloroethane), dioxane, $Et_2O$ (diethylether), $CH_3CN$, EtOAc (ethyl acetate), DMSO (dimethyl sulfoxide), DMF (dimethyl formamide), or toluene. In still other embodiments, the solvent is DCM, DCE, or toluene. In yet other embodiments, the solvent is a weak hydrogen bond acceptor.

In some embodiments, the amount of the organic molecule with at least one alkene (e.g., in (a) or in (b)) can be any suitable amount including but not limited to about 0.01 mmol, about 0.05 mmol, about 0.1 mmol, about 0.2 mmol, about 0.3 mmol, about 0.4 mmol, about 0.5 mmol, about 1 mmol, about 2 mmol, about 3 mmol, about 4 mmol, about 5 mmol, about 6 mmol, about 7 mmol, about 8 mmol, about 9 mmol, about 10 mmol, about 12 mmol, about 15 mmol, about 20 mmol, about 30 mmol, about 50 mmol, about 70 mmol, at least about 0.01 mmol, at least about 0.1 mmol, at least about 1 mmol, no more than about 1 mmol, no more than about 10 mmol, no more than about 15 mmol, no more than about 30 mmol, or no more than about 70 mmol. In some embodiments, the amount of the organic molecule with at least one alkene (e.g., in (a) or in (b)) can be any suitable amount including but not limited to about 0.001 M, about 0.01 M, about 0.05 M, about 0.1 M, about 0.2 M, about 0.3 M, about 0.4 M, about 0.5 M, about 0.6 M, about 0.7 M, about 0.8 M, about 0.9 M, about 1.0 M, about 1.5 M, about 2.0 M, about 2.5 M, about 3.0 M, about 4.0 M, about 5.0 M, about 6.0 M, about 7.0 M, about 8.0 M, about 9.0 M, about 10.0 M, at least about 0.001 M, at least about 0.01 M, at least about 0.05 M, at least about 0.1 M, no more than about 10.0 M, no more than about 7.0 M, no more than about 5.0 M, no more than about 3.0 M, or no more than about 1.0 M.

In other embodiments, in step (b) the composition of (a) (e.g., prior to contacting) can be at any suitable temperature including but not limited to about −5° C., about −2° C., about 0° C., about 2° C., about 5° C., at least about −5° C., at least about −2° C., no more than about 5° C., no more than about 2° C., no more than about 0° C., or no more than about −2° C.

In some embodiments, the contacting can occur under any suitable pressure including but not limited to about 0.1 atm, about 0.5 atm, about 1.0 atm, about 1.5 atm, about 2.0 atm, at least about 0.1 atm, at least about 0.5 atm, no more than about 1.5 atm, or no more than about 2.0 atm. The pressure can be the same or different in each step, if there are multiple steps in the method.

In some embodiments, the composition of (a) is added to a catalyst of Formula (I) in one portion, two portion, three portions, five portions, at least two portions, at least five portions, or no more than five portions. In other embodiments, the catalyst of Formula (I) is added to the composition of (a) in one portion, two portion, three portions, five portions, at least two portions, at least five portions, or no more than five portions. In certain embodiments, the catalyst can be at any suitable temperature (e.g., prior to or when being added to a solution, or prior to or if a solution is being added to it) including but not limited to about room temperature (e.g., from about 20° C. to about 25° C.), about −10° C., about −5° C., about 0° C., about 10° C., about 15° C., about 20° C., about 25° C., about 30° C., about 35° C., about 40° C., about 50° C., about 55° C., about 60° C., about 70° C., about 80° C., no more than about 60° C., no more than about 50° C., at least about −10° C., at least about 10° C., or at least about 20° C. In other embodiments, the contacting (e.g., in step (b)) occurs by mixing, stirring, or shaking, any of which can occur at any suitable temperature including but not limited to about room temperature (e.g., from about 20° C. to about 25° C.), about −10° C., about −5° C., about 0° C., about 10° C., about 15° C., about 20° C., about 25° C., about 30° C., about 35° C., about 40° C., about 50° C., about 55° C., about 60° C., about 70° C., about 80° C., no more than about 60° C., no more than about 50° C., at least about −10° C., at least about 10° C., or at least about 20° C. In certain embodiments, the amount of time of contacting (e.g., in step (b)) can be any suitable time including but not limited to about 0.01 hours (h), about 0.1 h, about 0.2 h, about 0.3 h, about 0.4 h, about 0.5 h, about 0.6 h, about 0.7 h, about 0.8 h, about 0.9 h, about 1.0 h, about 1.5 h, about 2.0 h, about 3.0 h, about 4.0 h, about 5.0 h, about 10 h, about 15 h, about 18 h, about 20 h, about 25 h, about 30 h, about 40 h, about 50 h, about 100 h, at least about 0.01 h, at least about 0.1 h, at least about 0.5 h, no more than about 100 h, no more than about 20 h, no more than about 5.0 h, or no more than about 1 h. In some embodiments, the mole ratio of the catalyst of Formula (I) to the organic compound comprising one or more alkenes can be any suitable mole ratio including but not limited to about 0.001, about 0.01, about 0.05, about 0.1, about 0.2, about 0.3, about 0.4, about 0.5, about 0.6, about 0.7, about 0.8, about 0.9, about 1.0, about 1.5, about 2.0, about 2.5, about 3.0, about 4.0, about 5.0, about 10, about 20, at least about 0.001, at least about 0.01, at least about 0.1, at least about 0.5, no more than about 1.0, no more than about 5.0, or no more than about 20. In some instances, the reaction can be monitored using any suitable method including but not limited to using TLC.

In other embodiments, the reaction can be cooled (e.g., to about 0° C.). In still other embodiments, the reaction can be quenched using any suitable method such as but not limited to cooling or adding $CaCO_3$.

In certain embodiments of the methods for hydrofluorination, the product molecule can be optionally or further recovered. Recovery can occur using any suitable method including but not limited to one or more of HPLC (e.g., reverse phase), LC, filtration (e.g., through kieselguhr), precipitation, concentrated, centrifugation, column chromatography (e.g., size exclusion chromatography, ion exchange chromatography, or flash chromatography), use of silica gel, washings (e.g., one or more time with one or more solvents or solvent mixtures), or combinations thereof.

The presently-disclosed subject matter is further illustrated by the following specific but non-limiting examples. The following examples may include compilations of data that are representative of data gathered at various times during the course of development and experimentation related to the present invention.

EXAMPLES

Section 1. Materials and Methods $^1$H NMR and $^{13}$C NMR spectra were recorded at 400 MHz and 100 MHz respectively, using $CDCl_3$ as a solvent. The chemical shifts are reported in δ (ppm) values relative to $CHCl_3$ (δ 7.26 ppm for $^1$H NMR), multiplicities are indicated by s (singlet), d (doublet), t (triplet), q (quartet), p (pentet), h (hextet), m (multiplet) and br (broad). Coupling constants, J, are reported in Hertz.

Solvents like DCM (dichloromethane), $Et_2O$ (diethylether), Toluene, DMF (dimethyl formamide) were chemically dried using a commercial solvent purification system. Other solvents like DCE (1,2 dichloroethane), dioxane, EtOAc (ethyl acetate) and DMSO (dimethyl sulfoxide) were dried with activated 4 Å molecular sieves overnight. Anhydrous hydrogen fluoride gas cylinder was purchased from Synquest Laboratories Inc. $KHSO_4$ and $K_2SO_4$ were from Aldrich. DMPU-HF (1,3-Dimethyltetrahydropyrimidin-2 (1H)-one hydrofluoride) was freshly prepared by our lab and Py-HF (a mixture of 70% hydrogen fluoride and 30% pyridine) was purchased form Alfa Aesar. All other reagents and solvents were employed without further purification. The products were purified using a CombiFlash system. TLC was developed on Merck silica gel 60 F254 aluminum sheets and $KMnO_4$ stain was used for TLC developing. $KMnO_4$ stain was prepared by dissolving 1.5 g of $KMnO_4$, 10 g $K_2CO_3$, and 1.25 mL 10% NaOH in 200 mL water. All NMR solvents were purchased from Cambridge Isotope Laboratories, Inc.

Most of the substrates in the reactions were purchased or synthesized according to the literature. Therefore, we only used $^1$H NMR to confirm the identity of those known compounds.

Section 2. Preparation of $KHSO_4$—HF and $K_2SO_4$—HF Complexes $KHSO_4$ (2.93 g) was added into a long Teflon tube which was cooled to 0° C. HF (5.71 g) gas was then condensed into the Teflon tube under stirring. The obtained liquid was stored in a 30 mL HDPE bottle with a screw cap. It is bench stable, but for long term storage, it was stored in a 4° C. refrigerator.

$K_2SO_4$-14HF was prepared with the same way.

Section 3. Preparation of Alkene Substrates

Synthesized alkene substrates 1 (these substrates were synthesized and confirmed with the literature data by its NMRs).

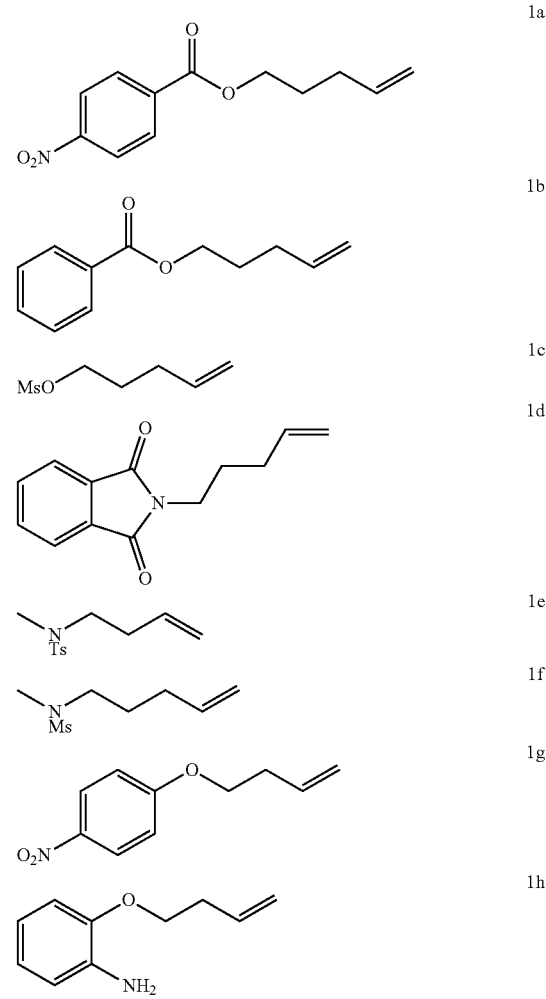

-continued
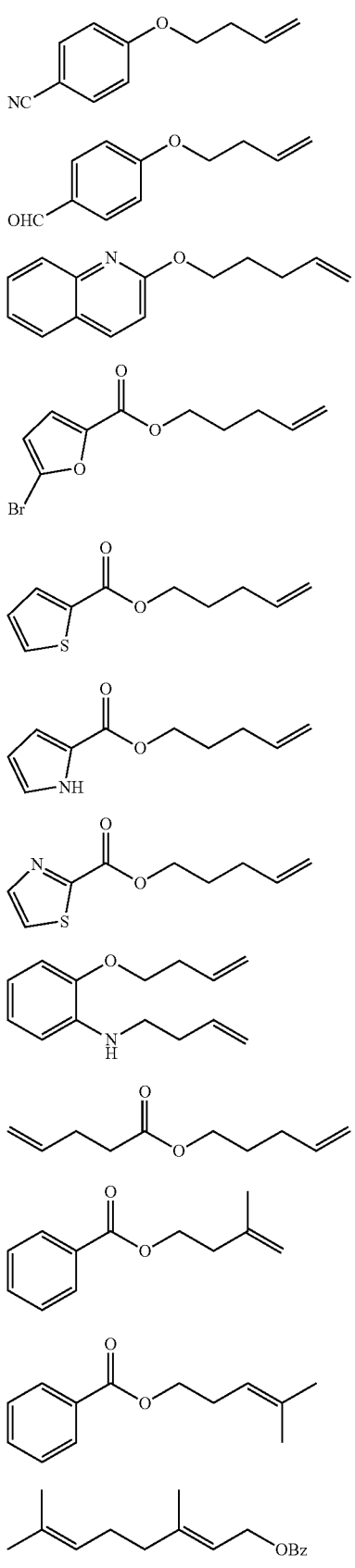
Alkene Substrates from Commercial Sources:
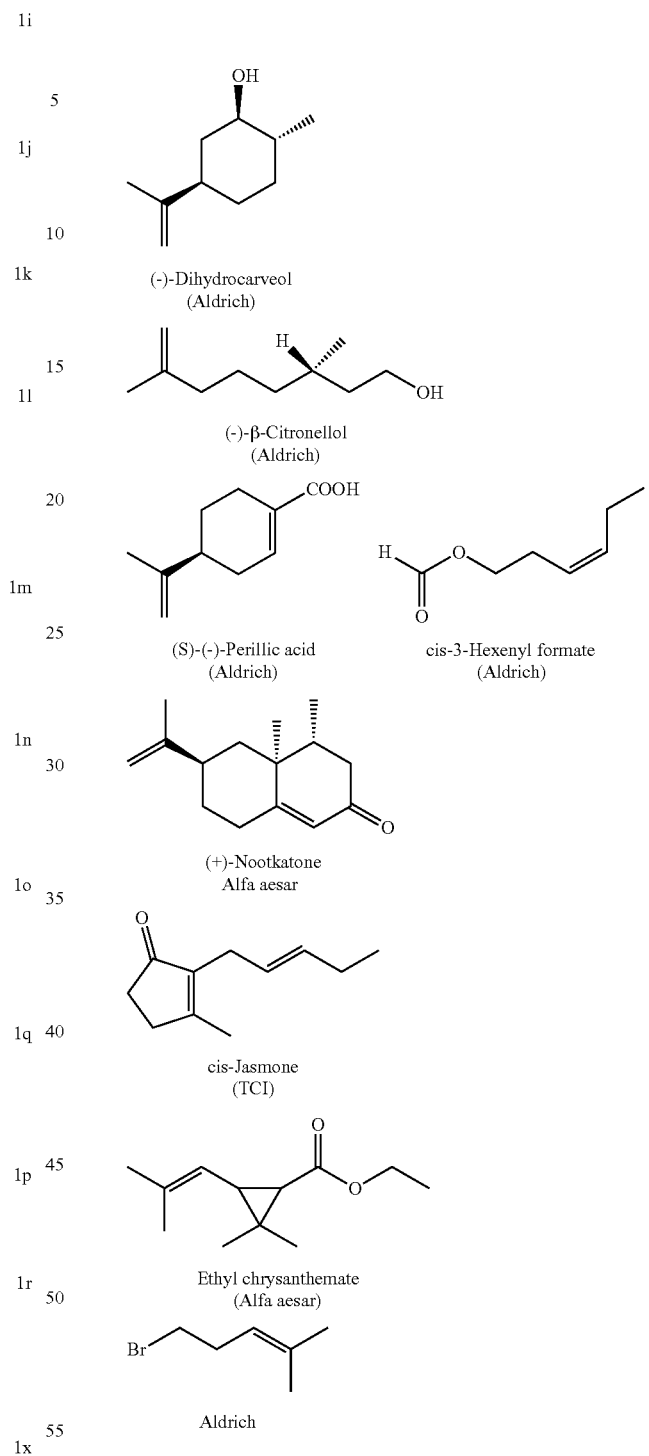
General Synthetic Procedure for Ester 1a, 1b, 1m, 1r, 1x, 1z
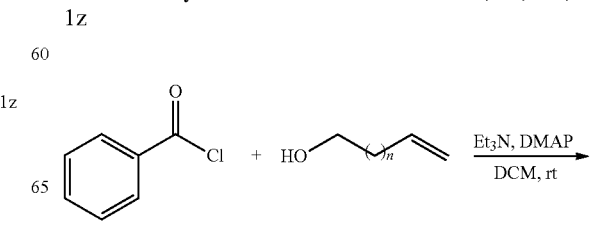

-continued

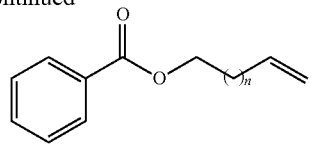

1a, 1b, 1m, 1r, 1x, 1z

A 20-mL vial fitted with a stirring bar was charged with alcohol (2 mmol), Et₃N (triethyl amine) (2 equiv) and dry DCM (10 mL). The mixture was cooled down to 0° C. and benzoyl chloride (1.2 equiv) and 5 mg DMAP (4-Dimethylaminopyridine) was then added sequentially. The mixture was stirred overnight and then was diluted with 50 mL DCM, washed with 1M aqueous HCl (2×20 mL), saturated NaHCO₃ (20 mL), brine (20 mL) sequentially. The organic layer was then dried with Na₂SO₄ and concentrated. The residue was purified with column chromatography to afford the desired ester.

General Synthetic Procedure for Ether 1g, 1h, 1i, 1j, 1q and Tosylamide 1e

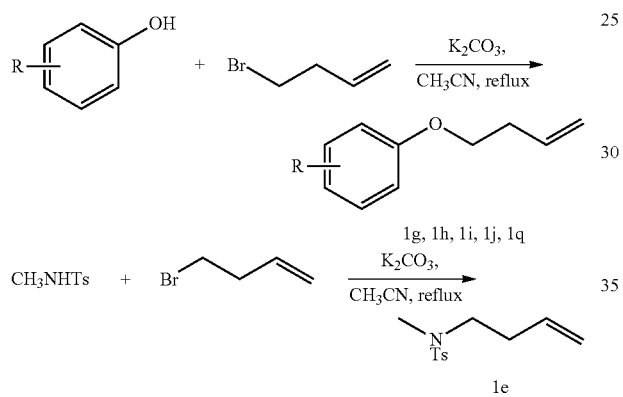

A 50-mL flask fitted with a stirring bar was charged with a solution of phenol (or CH₃NHTs, 2 mmol) and K₂CO₃ (1.5 equiv) in CH₃CN (15 mL), 4-bromo-1-butene was then added and the mixture was refluxed for 5 h. It was then cooled to rt and the solvent was removed in vacuo. The residue was concentrated and then partitioned between CH₂Cl₂ and water. The aqueous layer was extracted with CH₂Cl₂ (2×25 mL). The combined organic extracts were washed with water (2×20 mL), dried and concentrated in vacuo. The resulting residue was purified by silica gel flash chromatography to afford the desired ethers or tosylamides.

General Synthetic Procedure for 1d, 1f, 1k, 1n, 1o.

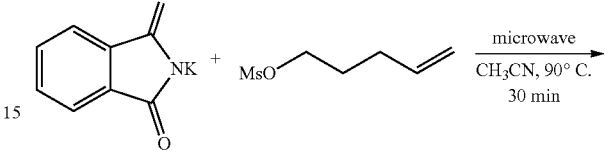

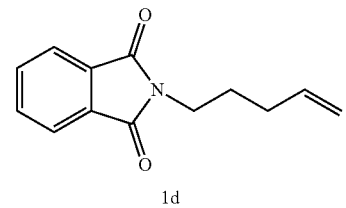

A 10-mL microwave tube fitted with a stirring bar was charged with a solution of potassium phthalimide (1.5 mmol), mesylate (1 equiv) in CH₃CN (2 mL). The mixture was stirred under microwave at 90° C. and hold for 30 mins. The reaction was concentrated and purified directly by silica gel flash chromatography to afford 1d.

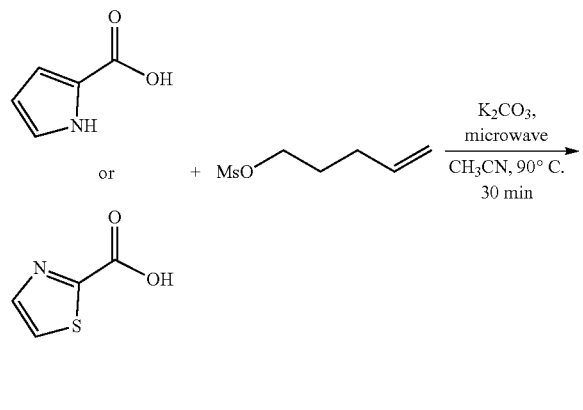

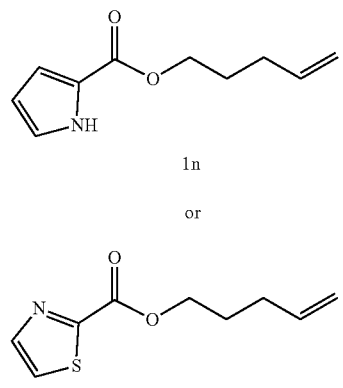

A 10-mL microwave tube fitted with a stirring bar was charged with a solution of acid starting material (1.5 mmol), K₂CO₃ (1.5 equiv), mesylate (1 equiv) in CH₃CN (2 mL).

The mixture was stirred under microwave at 90° C. and hold for 30 mins. The reaction was concentrated and purified directly by silica gel flash chromatography to afford 1n, 1o.

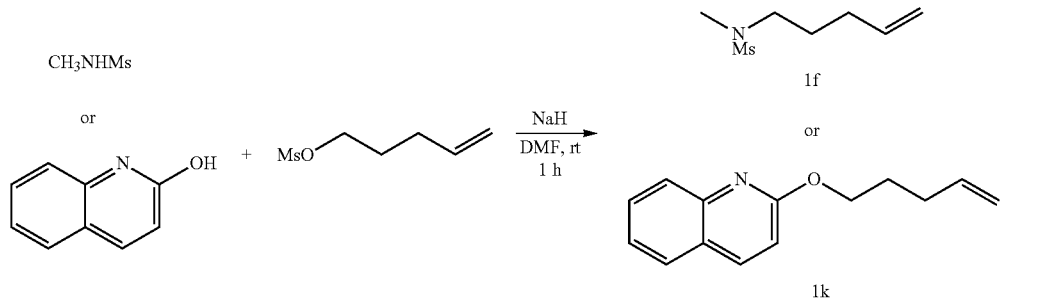

A 50-mL flask fitted with a stirring bar was charged with a solution of amide (2 mmol) in DMF (10 mL). The mixture was cooled down to ° C. and was added NaH (1.5 equiv). Mesylate was then added and the mixture was stirred at rt for 1 h. The reaction was quenched by 1M of NH$_4$Cl solution and diluted with CH$_2$Cl$_2$ (50 mL). After being washed with 5% LiCl aqueous solution (2×20 mL) and the aqueous layer was extracted with CH$_2$Cl$_2$ (20 mL). The combined organic extracts were washed with water (20 mL), dried and concentrated in vacuo. The resulting residue was purified by silica gel flash chromatography to afford 1f and 1k.

General Synthetic Procedure for Ester 1l, 1p

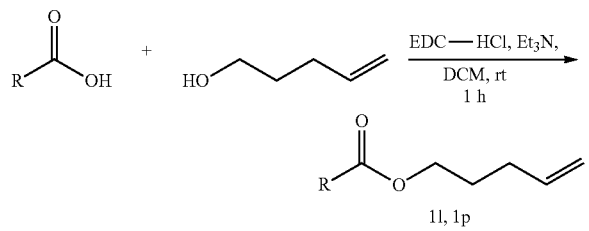

A 50-mL flask fitted with a stirring bar was charged with a solution of 4-penten-1-ol (2 mmol), EDCI (1.2 equiv), triethylamine (1.5 equiv), and DMAP (0.1 equiv) in dichloromethane (10 mL). 4-Pentenoic acid (1 equiv) was then added at 0° C. and the reaction mixture was stirred overnight at room temperature. After the reaction was complete, the resulting mixture was diluted with 50 mL DCM, washed by 1 N HCl (2×20 mL), 1 N aqueous NaHCO$_3$ (2×20 mL), and brine (1×20 mL). The organic layer was dried (Na$_2$SO$_4$) and evaporated in vacuo. The result residue was purified by column chromatography to afford the desired ester 1l, 1p.

Section 4. General Procedure for Hydrofluorination
4.1 Hydrofluorination of Mono-Substituted Alkenes.

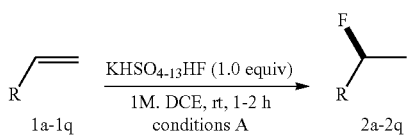

Conditions A.
An 8-mL PTFE vial fitted with a stirring bar was charged with dry DCE (0.2 mL) and alkene starting material (0.2 mmol). The mixture was cooled down to 0° C. and KHSO$_4$·13HF (54 μL, 1.0 equiv, 13.0 equiv based on HF) was then added in one portion at room temperature. The progress of reaction was monitored by TLC (visualized by KMnO$_4$ stain). Product usually showed a little higher polarity than the starting material on TLC (R$_f$ difference<0.1 in most cases). The reaction was then cooled down to 0° C. and quenched by CaCO$_3$. The resulting mixture was then stirred at room temperature and filtered through kieselguhr. The filtrate was concentrated and the residue was purified with flash chromatography.

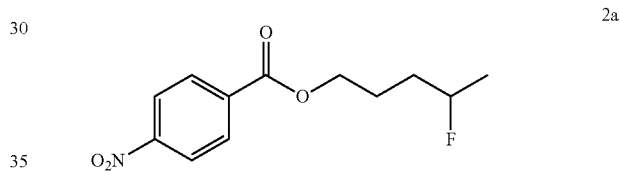

$^1$H NMR (400 MHz, CDCl$_3$) δ 8.38-8.26 (m, 2H), 8.25-8.19 (m, 2H), 4.74 (dm, J=48 Hz, 1H), 4.48-4.36 (m, 2H), 1.95 (m, 2H), 1.84-1.64 (m, 2H), 1.38 (dd, J=23.8, 6.2 Hz, 3H).
$^{13}$C NMR (100 MHz, CDCl$_3$) δ 164.62, 150.51, 135.61, 130.64, 123.52, 91.09, 89.44, 65.56, 33.45, 33.24, 24.48, 24.43, 21.09, 20.86.
$^{19}$F NMR (376 MHz, CDCl$_3$) δ -173.50--173.98 (m, 1F).
HRMS: (ESI$^+$) [M+H] cal. for C$_{12}$H$_{15}$FNO$_4$: 256.0985; found: 256.1981.

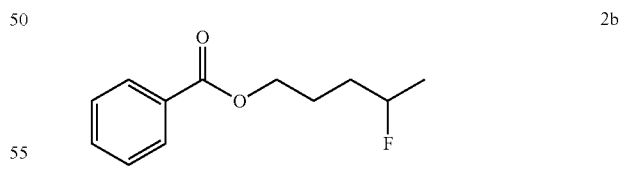

$^1$H NMR (400 MHz, CDCl$_3$) δ 8.03 (d, J=7.4 Hz, 2H), 7.55 (t, J=7.4 Hz, 1H), 7.43 (t, J=7.7 Hz, 2H), 4.84-4.58 (dm, J=48 Hz, 1H), 4.44-4.26 (m, 2H), 2.04-1.61 (m, 4H), 1.35 (dd, J=23.9, 6.2 Hz, 3H).
$^{13}$C NMR (100 MHz, CDCl$_3$) δ 166.55, 132.89, 130.24, 129.50, 128.33, 91.23, 89.59, 64.57, 33.56, 33.35, 24.56, 24.51, 21.11, 20.88.
$^{19}$F NMR (376 MHz, CDCl$_3$) δ -173.27--173.78 (m, 1F).
HRMS: (ESI$^+$) [M+H] cal. for C$_{12}$H$_{16}$FO$_2$: 211.1134; found: 211.1125.

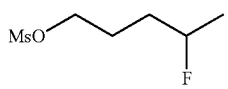

2c

¹H NMR (400 MHz, CDCl₃) δ 4.79-4.56 (dm, J=52.0 Hz, 1H), 4.33-4.17 (m, 2H), 3.00 (s, 3H), 2.00-1.63 (m, 4H), 1.34 (dd, J=23.9, 6.2 Hz, 3H).
¹³C NMR (100 MHz, CDCl₃) δ 91.01, 89.36, 69.60, 37.35, 32.83, 32.62, 25.07, 25.03, 21.07, 20.84.
¹⁹F NMR (376 MHz, CDCl₃) δ −174.16 (m, 1F).
HRMS: (ESI⁺) [M+NH₄] cal. for C₆H₁₇FNO₃S: 202.0908; found: 202.0904.

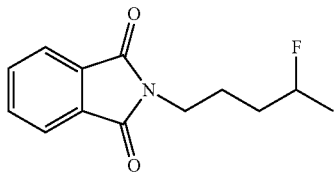

2d

¹H NMR (400 MHz, CDCl₃) δ 7.82 (dd, J=5.4, 3.2 Hz, 2H), 7.69 (dd, J=5.4, 3.2 Hz, 2H), 4.83-4.50 (dm, J=48 Hz, 1H), 3.80-3.61 (m, 2H), 1.94-1.42 (m, 4H), 1.29 (dd, J=23.9, 6.2 Hz, 3H).
¹³C NMR (100 MHz, CDCl₃) δ 168.37, 133.91, 132.03, 123.19, 91.08, 89.43, 37.60, 34.13, 33.92, 24.38, 24.34, 21.03, 20.81.
¹⁹F NMR (376 MHz, CDCl₃) δ −173.00−−173.50 (m, 1F).
HRMS: (ESI⁺) [M+H] cal. for C₁₃H₁₅FNO₂: 236.1087; found: 236.1076.

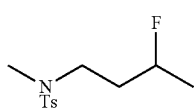

2e

¹H NMR (400 MHz, CDCl₃) δ 7.65 (d, J=8.0 Hz, 2H), 7.30 (d, J=8.0 Hz, 2H), 4.89-4.61 (dm, J=48 Hz, 1H), 3.20-2.97 (m, 2H), 2.72 (s, 3H), 2.41 (s, 3H), 1.81 (m, 2H), 1.34 (dd, J=24.0, 6.2 Hz, 3H).
¹³C NMR (100 MHz, CDCl₃) δ 143.38, 134.22, 129.66, 127.39, 89.20, 87.56, 46.71, 46.66, 35.60, 35.39, 35.35, 21.47, 21.05, 20.82.
¹⁹F NMR (376 MHz, CDCl₃) δ −175.08−−175.64 (m, 1F).
HRMS: (ESI⁺) [M+H] cal. for C₁₂H₁₉FNO₂S: 260.1121; found: 260.1109.

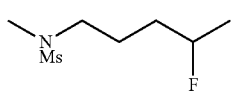

2f

¹H NMR (400 MHz, CDCl₃) δ 4.68 (dm, J=49.0 Hz, 1H), 3.22-3.07 (m, 2H), 2.83 (s, 3H), 2.77 (s, 3H), 1.81-1.59 (m, 4H), 1.32 (dd, J=23.9, 6.2 Hz, 3H).
¹³C NMR (100 MHz, CDCl₃) δ 91.20, 89.55, 49.57, 35.22, 34.42, 33.66, 33.45, 23.38, 23.34, 21.15, 20.92.
¹⁹F NMR (376 MHz, CDCl₃) δ −173.69−−174.22 (m, 1F).

HRMS: (ESI⁺) [M+H] cal. for C₇H₁₇FNO₂S: 198.0964; found: 198.0955.

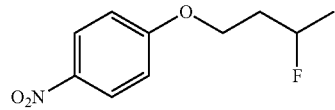

2g

¹H NMR (400 MHz, CDCl₃) δ 8.35-8.12 (m, 2H), 7.00-6.86 (m, 2H), 5.05-4.77 (dm, J=48 Hz, 1H), 4.30-4.04 (m, 2H), 2.18-1.96 (m, 2H), 1.41 (dd, J=24.0, 6.2 Hz, 3H).
¹³C NMR (100 MHz, CDCl₃) 163.76, 141.52, 125.91, 114.37, 88.30, 86.65, 64.64, 64.60, 36.44, 36.24, 21.24, 21.02.
¹⁹F NMR (376 MHz, CDCl₃) δ −176.27−−176.77 (m, 1F).
HRMS: (ESI⁺) [M+H] cal. for C₁₀H₁₃FNO₃: 214.0897; found: 214.0869.

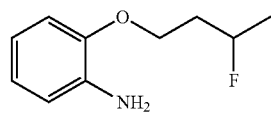

2h

¹H NMR (400 MHz, CDCl₃) δ 6.80 (dd, J=7.0, 5.7 Hz, 2H), 6.76-6.68 (m, 2H), 5.08-4.81 (dm, J=48 Hz, 1H), 4.25-4.04 (m, 2H), 3.79 (brs, 2H), 2.22-1.93 (m, 2H), 1.42 (dd, J=24.0, 6.2 Hz, 3H).
¹³C NMR (100 MHz, CDCl₃) δ 146.32, 136.27, 121.30, 118.48, 115.16, 111.58, 88.86, 87.22, 64.18, 64.13, 36.85, 36.64, 21.32, 21.10.
¹⁹F NMR (376 MHz, CDCl₃) δ −174.88−−175.42 (m).
HRMS: (ESI⁺) [M+H] cal. for C₁₀H₁₅FNO: 184.1138; found: 184.1130.

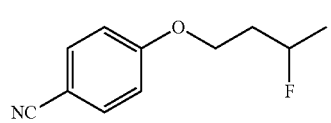

2i

¹H NMR (400 MHz, CDCl₃) δ 7.57 (d, J=8.9 Hz, 2H), 6.94 (d, J=8.9 Hz, 2H), 5.06-4.75 (dm, J=48 Hz, 1H), 4.30-3.98 (m, 2H), 2.25-1.89 (m, 2H), 1.41 (dd, J=24.0, 6.2 Hz, 3H).
¹³C NMR (100 MHz, CDCl₃) δ 162.02, 133.99, 119.18, 115.14, 104.03, 88.36, 86.72, 64.19, 64.15, 36.47, 36.26, 21.25, 21.02.
¹⁹F NMR (376 MHz, CDCl₃) δ −175.13−−176.24 (m, 1F).
HRMS: (ESI⁺) [M+H] cal. for C₁₁H₁₂FNNaO: 216.0801; found: 216.0793.

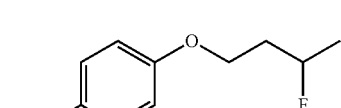

2j

¹H NMR (400 MHz, CDCl₃) δ 7.57 (d, J=8.9 Hz, 2H), 6.94 (d, J=8.9 Hz, 2H), 5.06-4.75 (dm, J=48 Hz, 1H), 4.30-3.98 (m, 2H), 2.25-1.89 (m, 2H), 1.41 (dd, J=24.0, 6.2 Hz, 3H).

$^{13}$C NMR (100 MHz, CDCl$_3$) δ 190.79, 163.79, 131.99, 129.97, 114.71, 88.43, 86.79, 64.19, 64.14, 36.54, 36.33, 21.26, 21.04.

$^{19}$F NMR (376 MHz, CDCl$_3$) δ −176.01−−176.55 (m, 1F).

HRMS: (ESI$^+$) [M+H] cal. for C$_{11}$H$_{14}$FO$_2$: 197.0978; found: 197.0971.

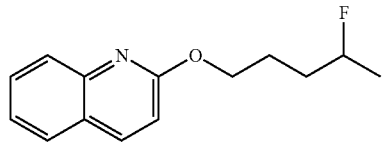

2k $^1$H NMR (400 MHz, CDCl$_3$) δ 7.97 (d, J=8.8 Hz, 1H), 7.81 (d, J=8.5 Hz, 1H), 7.70 (d, J=8.0 Hz, 1H), 7.60 (t, J=7.6 Hz, 1H), 7.36 (t, J=7.5 Hz, 1H), 6.88 (d, J=8.8 Hz, 1H), 4.87-4.63 (dm, J=52 Hz, 1H), 4.58-4.42 (m, 2H), 2.07-1.65 (m, 4H), 1.36 (dd, J=23.9, 6.2 Hz, 3H).

$^{13}$C NMR (100 MHz, CDCl$_3$) δ 162.10, 146.56, 138.64, 129.42, 127.38, 127.18, 125.02, 123.90, 113.15, 91.50, 89.86, 65.40, 33.70, 33.49, 24.78, 24.73, 21.13, 20.90.

$^{19}$F NMR (376 MHz, CDCl$_3$) δ −172.86−−173.35 (m, 1F).

HRMS: (ESI$^+$) [M+H] cal. for C$_{14}$H$_{17}$FNO: 234.1294; found: 234.1284.

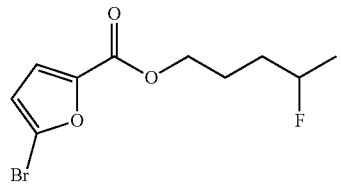

2l $^1$H NMR (400 MHz, CDCl$_3$) δ 7.25 (s, 1H), 7.11 (d, J=3.5 Hz, 2H), 6.45 (d, J=3.5 Hz, 2H), 4.82-4.57 (dm, J=48 Hz, 1H), 4.39-4.24 (m, 2H), 1.99-1.57 (m, 4H), 1.34 (dd, J=23.8, 6.2 Hz, 3H).

$^{13}$C NMR (100 MHz, CDCl$_3$) δ 157.61, 146.24, 127.50, 120.01, 113.87, 91.16, 89.52, 64.78, 33.36, 33.15, 24.50, 24.45, 21.07, 20.85.

$^{19}$F NMR (376 MHz, CDCl$_3$) δ −173.40−−173.88 (m, 1F).

HRMS: (ESI$^+$) [M+H] cal. for C$_{10}$H$_{13}$BrFO$_3$: 279.0032; found: 279.0020.

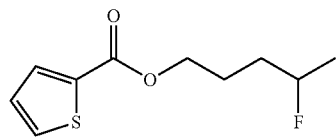

2m $^1$H NMR (400 MHz, CDCl$_3$) δ 7.78 (d, J=3.7 Hz, 1H), 7.54 (d, J=5.0 Hz, 1H), 7.09 (t, J=4.3 Hz, 1H), 4.71 (dm, J=48.0 Hz, 1H), 4.39-4.20 (m, 2H), 2.00-1.59 (m, 4H), 1.34 (dd, J=23.9, 6.1 Hz, 3H).

$^{13}$C NMR (100 MHz, CDCl$_3$) δ 162.19, 133.79, 133.34, 132.28, 127.71, 91.19, 89.54, 64.71, 33.47, 33.26, 24.54, 24.49, 21.09, 20.86.

$^{19}$F NMR (376 MHz, CDCl$_3$) δ −173.30−−173.77 (m, 1F).

HRMS: (ESI$^+$) [M+H] cal. for C$_{10}$H$_{14}$FO$_2$S: 217.0699; found: 217.0688.

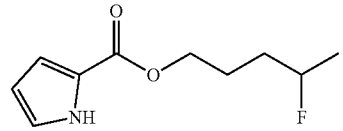

2n $^1$H NMR (400 MHz, CDCl$_3$) δ 9.20 (s, 1H), 6.95 (dt, J=4.1, 2.1 Hz, 1H), 6.92-6.87 (m, 1H), 6.29-6.20 (m, 1H), 4.81-4.58 (dm, J=52.0 Hz, 1H), 4.35-4.20 (m, 2H), 1.98-1.56 (m, 4H), 1.33 (dd, J=23.9, 6.2 Hz, 3H).

$^{13}$C NMR (100 MHz, CDCl$_3$) δ 162.19, 133.79, 133.34, 132.28, 127.71, 91.19, 89.54, 64.71, 33.47, 33.26, 24.54, 24.49, 21.09, 20.86.

$^{19}$F NMR (376 MHz, CDCl$_3$) δ −173.26−−173.74 (m, 1F).

HRMS: (ESI$^+$) [M+H] cal. for C$_{10}$H$_{15}$FNO$_2$: 200.1087; found: 200.1078.

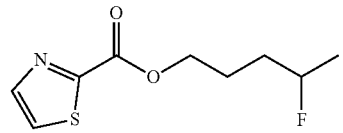

2o $^1$H NMR (400 MHz, CDCl$_3$) δ 8.02 (d, J=2.9 Hz, 1H), 7.62 (d, J=2.9 Hz, 1H), 4.70 (dm, J=48 Hz, 1H), 4.50-4.36 (m, 2H), 2.07-1.60 (m, 4H), 1.33 (dd, J=23.9, 6.2 Hz, 3H).

$^{13}$C NMR (100 MHz, CDCl$_3$) δ 159.98, 158.30, 144.98, 125.22, 91.11, 89.46, 66.11, 33.32, 33.11, 24.46, 24.41, 21.06, 20.83.

$^{19}$F NMR (376 MHz, CDCl$_3$) δ −173.50−−173.97 (m, 1F).

HRMS: (ESI$^+$) [M+H] cal. for C$_9$H$_{13}$FNO$_2$S: 218.0651; found: 218.0642.

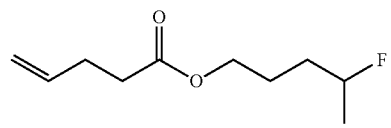

2p $^1$H NMR (400 MHz, CDCl$_3$) δ 5.88-5.74 (m, 1H), 5.03 (dd, J=21.9, 13.8 Hz, 2H), 4.67 (dm, J=48 Hz, 1H), 4.10 (m, 2H), 2.50-2.29 (m, 4H), 1.74 (m, 4H), 1.33 (dd, J=23.9, 6.1 Hz, 3H).

$^{13}$C NMR (100 MHz, CDCl$_3$) δ 173.04, 136.64, 115.47, 91.19, 89.54, 63.99, 33.51, 33.44, 33.23, 28.86, 24.44, 24.40, 21.06, 20.84.

$^{19}$F NMR (376 MHz, CDCl$_3$) δ −173.26−−173.78 (m, 1F).

HRMS: (ESI$^+$) [M+H] cal. for C$_{10}$H$_{18}$FO$_2$: 189.1291; found: 189.1283.

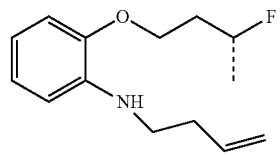

2q $^1$H NMR (400 MHz, CDCl$_3$) δ 6.88 (t, J=7.5 Hz, 1H), 6.78 (d, J=7.8 Hz, 1H), 6.64 (dd, J=13.1, 7.7 Hz, 2H), 5.85

(td, J=17.0, 7.0 Hz, 1H), 5.20-5.07 (m, 2H), 5.04-4.81 (dm, J=48 Hz, 1H), 4.25 (s, 1H), 4.19-4.02 (m, 2H), 3.20 (t, J=6.6 Hz, 2H), 2.43 (q, J=6.7 Hz, 2H), 2.21-1.81 (m, 2H), 1.41 (dd, J=24.0, 6.2 Hz, 3H).

$^{13}$C NMR (100 MHz, CDCl$_3$) δ 145.85, 138.34, 135.98, 121.52, 116.85, 116.36, 110.59, 110.07, 88.83, 87.19, 64.17, 64.12, 42.47, 36.83, 36.62, 33.66, 21.30, 21.08.

$^{19}$F NMR (376 MHz, CDCl$_3$) δ −174.74--−175.27 (m, 1F).

HRMS: (ESI$^+$) [M+H] cal. for C$_{14}$H$_{21}$FNO: 238.1607; found: 238.1597.

4.2 Hydrofluorination of Disubstituted Alkenes.

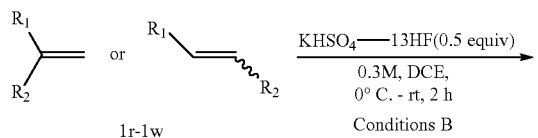

Conditions B.

An 8-mL PTFE vial fitted with a stirring bar was charged with dry DCE (0.6 mL) and alkene starting material (0.2 mmol). The mixture was cooled down to 0° C. KHSO$_4$-13HF (27 µL, 0.5 equiv, 6.5 equiv based on HF) was then added in one portion at rt. The progress of reaction was monitored by TLC (visualized by KMnO$_4$ stain). Product usually showed a little higher polarity than the starting material on TLC (R$_f$ difference<0.1). The reaction was then cooled down to 0° C. and quenched by CaCO$_3$. The resulting mixture was then stirred at room temperature and filtered through kieselguhr. The filtrate was concentrated and the residue was purified with flash chromatography.

2r

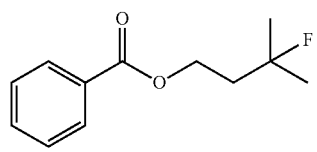

$^1$H NMR (400 MHz, CDCl$_3$) δ 8.05 (dd, J=8.4, 1.3 Hz, 1H), 7.62-7.53 (m, 1H), 7.45 (td, J=7.5, 1.6 Hz, 2H), 4.49 (t, J=6.8 Hz, 2H), 2.14 (dt, J=19.4, 6.8 Hz, 2H), 1.47 (d, J=21.5 Hz, 6H).

$^{13}$C NMR (100 MHz, CDCl$_3$) δ 166.47, 132.93, 130.16, 129.50, 128.35, 95.08, 93.43, 60.93, 60.87, 39.93, 39.69, 27.18, 26.94.

$^{19}$F NMR (376 MHz, CDCl$_3$) δ −138.14 (td, J=41.3, 20.5 Hz, 1F).

HRMS: (ESI$^+$) [M+H] cal. for C$_{12}$H$_{16}$FO$_2$: 211.1134; found: 211.1124.

2s

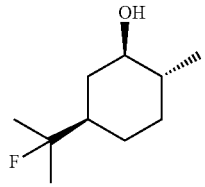

$^1$H NMR (400 MHz, CDCl$_3$) δ 3.14 (td, J=10.3, 4.2 Hz, 1H), 2.03 (dd, J=7.4, 4.6 Hz, 1H), 1.79-1.67 (m, 2H), 1.66-1.51 (m, 2H), 1.28 (d, J=22.0 Hz, 6H), 1.12-0.89 (m, 6H).

$^{13}$C NMR (100 MHz, CDCl$_3$) δ 97.89, 96.24, 76.25, 46.48, 46.26, 40.00, 36.40, 36.35, 32.80, 26.56, 26.51, 24.57, 24.53, 24.32, 24.28, 18.21.

$^{19}$F NMR (376 MHz, CDCl$_3$) δ −139.48 (dtd, J=44.1, 22.1, 11.5 Hz, 1F).

HRMS: (ESI$^+$) [M+H] cal. for C$_{10}$H$_{20}$FO: 175.1498; found: 175.1478.

2t

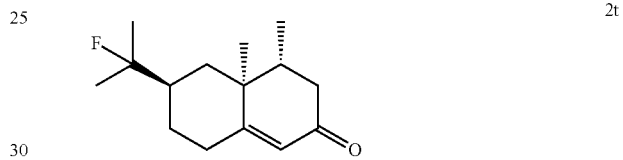

$^1$H NMR (400 MHz, CDCl$_3$) δ 5.74 (s, 1H), 2.52-2.41 (m, 1H), 2.40-2.30 (m, 1H), 2.30-2.16 (m, 2H), 2.04-1.87 (m, 4H), 1.30 (dd, J=22.1, 9.6 Hz, 6H), 1.24-1.12 (m, 1H), 1.07 (s, 3H), 1.00 (d, J=13.0 Hz, 1H), 0.96 (d, J=6.7 Hz, 3H).

$^{13}$C NMR (100 MHz, CDCl$_3$) δ 199.51, 170.06, 124.65, 97.97, 96.30, 42.64, 42.41, 42.04, 40.49, 39.27, 39.22, 39.00, 32.63, 27.54, 27.48, 24.80, 24.55, 24.17, 23.92, 16.80, 14.94.

$^{19}$F NMR (376 MHz, CDCl$_3$) δ −139.13--−140.13 (m, 1F).

HRMS: (ESI$^+$) [M+H] cal. for C$_{15}$H$_{24}$FO: 239.1811; found: 239.1799.

2u

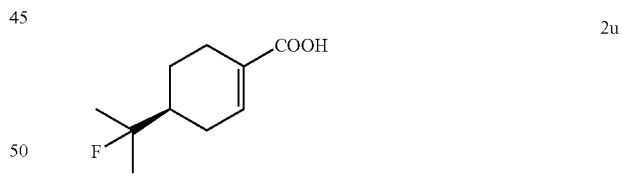

Isomer Ratio: (6:1)

$^1$H NMR (400 MHz, CDCl$_3$) δ 7.10 (s, 1H), 7.00 (s, 0.16H), 2.51 (d, J=19.3 Hz, 1H), 2.44-2.29 (m, 1.6H), 2.23-2.11 (m, 1.1H), 2.01 (dd, J=35.6, 15.0 Hz, 2.2H), 1.87 (m, 0.2H), 1.82-1.70 (m, 1H), 1.33 (dd, J=21.9, 3.5 Hz, 6H), 1.25 (dd, J=12.2, 7.0 Hz, 1H), 1.04 (t, J=9.2 Hz, 0.19H), 1.01-0.91 (m, 1H).

$^{13}$C NMR (100 MHz, CDCl$_3$) δ 172.99, 172.45, 155.86, 139.48, 138.60, 136.92, 130.32, 127.26, 126.54, 123.89, 116.44, 115.89, 35.16, 34.31, 34.24, 28.04, 25.58, 25.50, 23.66, 21.31, 21.00, 20.80.

$^{19}$F NMR (376 MHz, CDCl$_3$) δ −141.17--−142.90 (m, 1F), −160.86--−161.76 (m, 0.16F).

HRMS: (ESI$^+$) [M+H] cal. for C$_{10}$H$_{16}$FO$_2$: 187.1134; found: 187.1132.

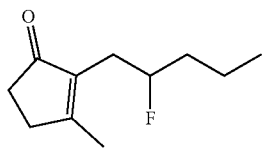

2v

Isomer Ratio: (1.3:1)
$^1$H NMR (400 MHz, CDCl$_3$) δ 4.61 (dm, J=48 Hz, 1H), 4.30 (dm, J=48 Hz, 0.75H), 2.49 (s, 3.5H), 2.40-2.32 (m, 4.1H), 2.32-2.22 (m, 1.1H), 2.19 (t, J=7.1 Hz, 2.2H), 2.05 (m, 5.3H), 1.76-1.36 (m, 8H), 1.28 (dd, J=24.0, 6.2 Hz, 3H), 0.94 (t, J=7.4 Hz, 2H).
$^{13}$C NMR (100 MHz, CDCl$_3$) δ 209.58, 170.89, 170.52, 140.14, 139.54, 95.89, 94.22, 91.62, 89.99, 36.74, 36.53, 34.29, 33.02, 32.82, 31.59, 31.53, 28.15, 27.94, 23.92, 23.87, 22.66, 21.07, 20.84, 18.90, 18.86, 17.24, 17.15, 9.37, 9.31.
$^{19}$F NMR (376 MHz, CDCl$_3$) δ −172.13−−172.79 (m, 1F), −182.88−−183.58 (m, 0.75F).
HRMS: (ESI$^+$) [M+H] cal. for C$_{11}$H$_{17}$FNaO: 207.1161; found: 207.1153.

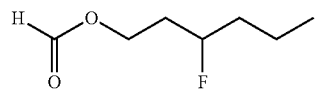

2w

Isomer Ratio: (2:1)
$^1$H NMR (400 MHz, CDCl$_3$) δ 8.03 (s, 1.29H), 4.78-4.52 (dm, J=48 Hz, 1H), 4.49-4.31 (dm, J=48 Hz, 0.5H), 4.23-4.13 (m, 3H), 1.90-1.36 (m, 9H), 1.32 (d, J=6.2 Hz, 1.5H), 1.26 (d, J=6.2 Hz, 1.5H), 0.94 (t, J=7.5 Hz, 1.5H).
$^{13}$C NMR (100 MHz, CDCl$_3$) δ 172.99, 172.45, 155.86, 139.48, 138.60, 136.92, 130.32, 127.26, 126.54, 123.89, 116.44, 115.89, 35.16, 34.31, 34.24, 28.04, 25.58, 25.50, 23.66, 21.31, 21.00, 20.80.
$^{19}$F NMR (376 MHz, CDCl$_3$) δ −172.99−−173.31 (m, 1F), −182.13−−182.73 (m, 0.5F).
HRMS: (ESI$^+$) [M+H] cal. for C$_7$H$_{14}$FO$_2$: 149.0978; found: 149.0231.

4.3 Hydrofluorination of Trisubstituted Alkenes.

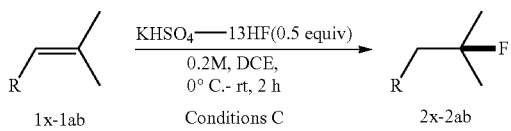

Conditions C.
An 8-mL PTFE vial fitted with a stirring bar was charged with dry DCE (1 mL) and alkene starting material (0.2 mmol). The mixture was cooled down to 0° C. KHSO$_4$-13HF (27 µL, 0.5 equiv, 6.5 equiv based on HF) was then added in one portion and the reaction stirred at rt. The reaction was monitored by TLC (visualized by KMnO$_4$ stain). Product usually showed a little higher polarity than the starting material on TLC (R$_f$ difference<0.1). The reaction was then cooled down to 0° C. and quenched by CaCO$_3$. The resulting mixture was then stirred at room temperature and filtered through kieselguhr. The filtrate was concentrated and the residue was purified with flash chromatography.

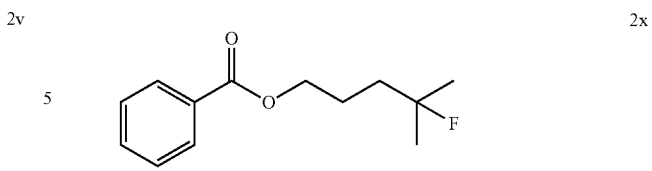

2x $^1$H NMR (400 MHz, CDCl$_3$) δ 8.06-7.96 (m, 2H), 7.54 (t, J=7.4 Hz, 1H), 7.42 (t, J=7.6 Hz, 2H), 4.32 (t, J=6.5 Hz, 2H), 1.94-1.81 (m, 2H), 1.80-1.65 (m, 2H), 1.36 (d, J=21.3 Hz, 6H).
$^{13}$C NMR (100 MHz, CDCl$_3$) δ 166.53, 132.87, 130.28, 129.50, 128.32, 95.93, 94.29, 64.95, 37.84, 37.61, 26.74, 26.50, 23.46, 23.41.
$^{19}$F NMR (376 MHz, CDCl$_3$) δ −138.94 (dt, J=41.2, 21.0 Hz, 1F).
HRMS: (ESI$^+$) [M+H] cal. for C$_{13}$H$_{18}$FO$_2$: 225.1291; found: 225.1116.

2y $^1$H NMR (400 MHz, CDCl$_3$) δ 3.42 (t, J=6.7 Hz, 2H), 2.02-1.91 (m, 2H), 1.81-1.67 (m, 2H), 1.34 (d, J=21.3 Hz, 6H).
$^{13}$C NMR (100 MHz, CDCl$_3$)$^{13}$C NMR (100 MHz, cdcl$_3$) δ 95.90, 94.25, 45.89, 40.00, 39.77, 34.28, 33.92, 33.44, 29.73, 27.35, 27.30, 26.79, 26.55.
$^{19}$F NMR (376 MHz, CDCl$_3$) δ −138.97 (dt, J=42.0, 21.0 Hz, 1F).
The above NMR data accords with the reference.[1]

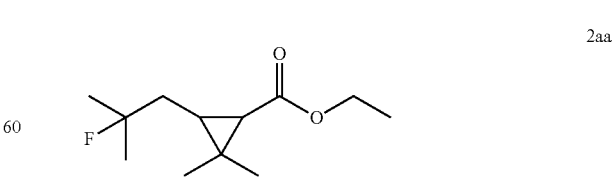

2z $^1$H NMR (400 MHz, CDCl$_3$) δ 8.04 (d, J=7.9 Hz, 2H), 7.54 (t, J=7.3 Hz, 1H), 7.42 (t, J=7.6 Hz, 2H), 5.47 (t, J=7.0 Hz, 1H), 4.83 (d, J=7.0 Hz, 2H), 2.06 (t, J=6.5 Hz, 2H), 1.75 (s, 3H), 1.58 (m, 2H), 1.54 (m, 2H), 1.35 (s, 3H), 1.30 (s, 3H).
$^{13}$C NMR (100 MHz, CDCl$_3$) δ 166.63, 142.06, 132.78, 130.43, 129.55, 128.35, 128.27, 118.66, 96.41, 94.78, 61.79, 40.95, 40.72, 39.59, 26.76, 26.51, 21.84, 21.79, 16.37.
$^{19}$F NMR (376 MHz, CDCl$_3$) δ −137.31−−138.08 (m, 1F).
HRMS: (ESI$^+$) [M+NH$_4$] cal. for C$_{17}$H$_{27}$FNO$_2$: 296.2026; found: 296.2013.

2aa $^1$H NMR (400 MHz, CDCl$_3$) δ 4.17-4.00 (m, 2H), 1.81-1.55 (m, 2H), 1.44-1.39 (m, 1H), 1.37 (d, J=3.8 Hz, 3H), 1.36-1.28 (m, 3H), 1.27-1.23 (m, 3H), 1.21 (s, 3H), 1.20-1.15 (m, 1H), 1.11 (s, 3H).

$^{13}$C NMR (100 MHz, CDCl$_3$) δ 172.52, 96.23, 94.57, 60.18, 39.79, 39.56, 32.85, 28.78, 28.72, 26.80, 26.63, 26.56, 26.39, 21.61, 20.57, 14.37.

$^{19}$F NMR (376 MHz, CDCl$_3$) δ −136.32−−136.82 (m, 1F), −139.25 (dt, J=43.1, 21.6 Hz, 0.07F).

HRMS: (ESI$^+$) [M+H] cal. for C$_{12}$H$_{22}$FO$_2$: 217.1604; found: 217.1594.

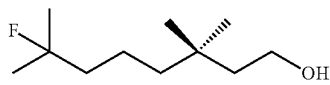

2ab $^1$H NMR (400 MHz, CDCl$_3$) δ 3.73-3.58 (m, 2H), 1.66-1.50 (m, 4H), 1.46-1.24 (m, 10H), 1.20-1.07 (m, 2H), 0.89 (d, J=6.5 Hz, 3H).

$^{13}$C NMR (100 MHz, CDCl$_3$) δ 96.58, 94.95, 61.08, 41.69, 41.46, 39.85, 37.31, 29.38, 26.78, 26.69, 26.54, 26.44, 21.29, 21.24, 19.51.

$^{19}$F NMR (376 MHz, CDCl$_3$) δ −137.33 (td, J=41.4, 20.7 Hz, 1F).

HRMS: (ESI$^+$) [M+Na] cal. for C$_{10}$H$_{21}$FNaO: 199.1474; found: 199.1688.

Results and Discussion

As an example of Formula (I), the bisulfate anion appears to exhibit a bifunctional behavior: its —OH terminus can be strongly acidic (e.g., pKa=1.9) and its ionic —O$^-$ M$^+$ (e.g., K$^+$) terminus is a strong hydrogen bond acceptor. Thus, MHSO$_4$ (e.g., KHSO$_4$) appears to form a hydrogen bond network with multiple molecules of HF. This hydrogen bonding interaction appears to achieve two aims: i) it condenses gaseous HF and forms a stable liquid at room temperature; ii) it enhances the nucleophilicity of HF. Without being bound by theory, in the hydrofluorination of alkenes, we believe that the acid terminus activates the alkene substrate while the H-bond acceptor terminus directs the nucleophilic attack of HF towards the acid-activated alkene, thereby accomplishing high acidity/high nucleophilicity and HF condensation simultaneously.

MHSO$_4$ (e.g., KHSO$_4$) formed a stable liquid at room temperature with large amounts of HF. In some instances, this HF mole content is higher than that of any commercial reagents, including Olah's reagent (pyridine-9HF) and DMPU-12HF. Without being bound by theory, the high HF affinity of MHSO$_4$ (e.g., KHSO$_4$) could be rationalized using Hunter and coworkers' recently reported H-bond scale (parameter β) (PIKE et al., "H-Bond Acceptor Parameters for Anions" J. Am. Chem. Soc. (2017) Vol. 139, pp. 6700-6706). In this scale, the hydrogen bonding basicities of anionic species were found to be higher than those of neutral organic HBAs (hydrogen bond acceptors). Hydrogen bond basicity (measured by β) of HSO$_4^-$ is comparable to the best neutral HBA, such as R$_3$PO, and is higher than that of DMPU. In some instances, an additional advantage of MHSO$_4$ (e.g., KHSO$_4$) is its low cost, ready availability and easy removal in aqueous work-up.

We used the hydrofluorination of alkene 1a as one model reaction (Table 1). As expected, Olah's reagent (pyridine-9HF, HF 70 wt/wt %) failed (Table 1, entry 1). And the more acidic DMPU-12HF (HF 65 wt/wt %) reagent gave only trace amounts of hydrofluorination product 2a (Table 1, entry 2). KHSO$_4$-13HF (HF 68 wt/wt %) produced 2a, albeit in moderate yield (Table 1, entry 3). The K$_2$SO$_4$-14HF complex (Table 1, entry 4) was less effective: a larger excess of HF was present and an extended reaction time was needed. The yield of the product was improved using 1,2-dichloroethane (DCE) as solvent (Table 1, entry 5). We also prepared an HF complex with lower HF content (KHSO$_4$-8HF), but its reaction was slower compared with KHSO$_4$-13HF (Table 1, entry 6). The HF complex of another bifunctional salt, KH$_2$PO$_4$, was also investigated but it gave less conversion (Table 1, entry 7). This result demonstrated that the acidic terminus of KHSO$_4$ may perhaps play a role in the addition of HF. Of all the solvents screened (Table 1, entries 8-13) toluene and DCE showed similar satisfactory results, but we selected DCE because of improved substrate solubility. Extending the reaction time to 2 hours in DCE further improved the yield to 83% (Table 1, entry 15).

TABLE 1

Reaction Condition Optimization of Hydrofluorination of Alkenes.$^a$

| Entry | Solvent | HF complex | Conditions | 1a/2a (%)$^b$ |
|---|---|---|---|---|
| 1 | DCM | Pyridine-9HF | 0° C.-rt, 0.5 h | 100/0 |
| 2 | DCM | DMPU—12HF | 0° C.-rt, 0.5 h | 96/4 |
| 3 | DCM | KHSO$_4$—13HF | 0° C.-rt, 0.5 h | 57/43 |
| 4 | DCM | K$_2$SO$_4$—14HF | 0° C.-rt, 18 h | 84/16 |
| 5 | DCE | KHSO$_4$—13HF | 0° C.-rt, 0.5 h | 29/71 |
| 6 | DCE | KHSO$_4$—8HF | 0° C.-rt, 0.5 h | 58/32 |
| 7 | DCE | KH$_2$PO$_4$—9HF | 0° C.-rt, 0.5 h | 100/0 |
| 8 | dioxane | KHSO$_4$—13HF | 0° C.-rt, 0.5 h | 100/0 |
| 9 | Et$_2$O | KHSO$_4$—13HF | 0° C.-rt, 0.5 h | 100/0 |
| 10 | CH$_3$CN | KHSO$_4$—13HF | 0° C.-rt, 0.5 h | 100/0 |
| 11 | EtOAc | KHSO$_4$—13HF | 0° C.-rt, 0.5 h | 100/0 |
| 12 | DMSO | KHSO$_4$—13HF | 0° C.-rt, 0.5 h | 100/0 |
| 13 | DMF | KHSO$_4$—13HF | 0° C.-rt, 0.5 h | 100/0 |
| 14 | toluene | KHSO$_4$—13HF | 0° C.-rt, 0.5 h | 26/74 |
| 15 | DCE | KHSO$_4$—13HF | 0° C.-rt, 2 h | 3/83 |

$^a$Reaction conditions: 1 (0.2 mmol), HF complex (1 equiv), solvent (0.2 mL), 0° C. to rt.
$^b$GC-MS yield.

After establishing the optimal conditions for the hydrofluorination of alkenes, we explored the scope of this protocol (Table 2). First, we investigated the fluorination of mono-substituted alkenes (Table 2a). As shown in Table 2a, a wide range of functional groups such as esters (2a, 2b), sulfonate (2c), amides (2d, 2e, 2f), ethers (2g, 2h, 2i, 2j), nitro (2g), nitrile (2i), aldehyde (2j) and amine (2h) were well tolerated. Also, alkenes with various heterocycles such as quinoline (2k), furan (2l), thiophene (2m), pyrrole (2n) and thiazole (2o) also gave good to excellent yields.

When this protocol was applied to more reactive disubstituted alkenes, that is, a more dilute solution (0.3 M) and less equivalents of KHSO$_4$—HF (conditions B) (Table 2b). Because disubstituted alkenes are commonly found in natural products, we screened natural products featuring various functionalities. We were glad to find that a natural product with a secondary alcohol, such as (−)-dihydrocarveol, tolerated the acidic reaction conditions and gave a moderate yield of the product (Table 2b, 2s). Nootkatone, possessing an α, β unsaturated ketone moiety, and perillic acid, exhibiting a carboxylic acid moiety, also gave products 2t and 2u, respectively, in good yields. Similarly, 1,2-disubstituted substrates gave the regioisomeric products 2v, 2w in good yields.

The reaction of our new $KHSO_4$—HF reagent was also investigated with the more reactive trisubstituted alkenes (Table 2c). The reaction concentration needed to be diluted further to 0.2 M to avoid the decomposition of the products (conditions C). The reaction of geranyl benzoate showed good chemoselectivity, with the more electron rich double bond participating in the hydrofluorination (2z). The cyclopropane motif remained intact after the reaction with ethyl chrysanthemate (2aa). Reaction with (−)-β-citronellol, which bears a primary alcohol functionality, also gave a good yield of the product 2ab.

TABLE 2

Scope of Hydrofluorination of Alkenes.

a) Hydrofluorination of Monosubstituted Alkenes.

$$\underset{1}{R\diagup\!\!\!=} \xrightarrow[\text{DCE (1M), rt, 1-2 h}]{\underset{\text{conditions A}}{KHSO_4\text{—}13HF\ (1.0\ \text{equiv})}} \underset{2}{R\diagup\!\!\!\diagdown F}$$

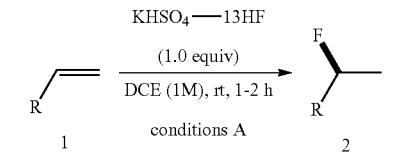

2a, 83%

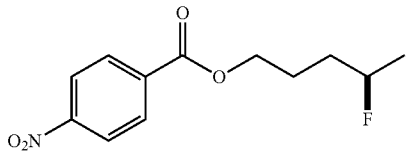 [SMILES: C[C@@H](F)CCCOC(=O)c1ccc([N+](=O)[O-])cc1]

2b, 85%

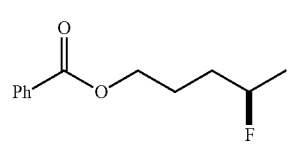

2c, 82%

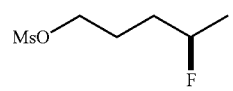

2d, 71%[a]

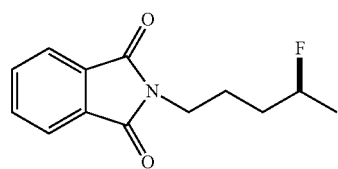 [SMILES: C[C@H](F)CCCN1C(=O)c2ccccc2C1=O]

2e, 56%[b]

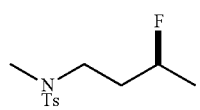 [SMILES: Cc1ccc(S(=O)(=O)N(C)CC[C@H](C)F)cc1]

2f, 31%[c]

TABLE 2-continued
Scope of Hydrofluorination of Alkenes.
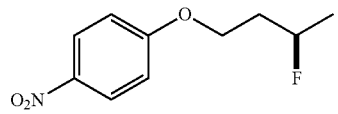
2g, 81%
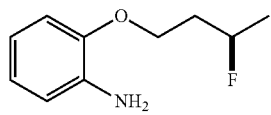
2h, 73%
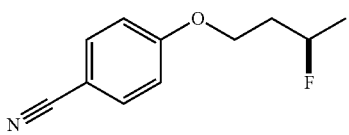
2i, 59%
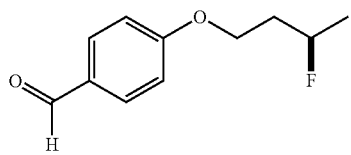
2j, 71%
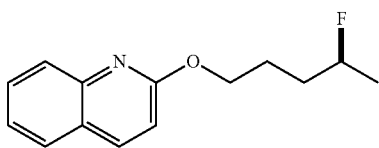 [SMILES: C[C@H](F)CCCOc1ccc2ccccc2n1]
2k, 76%[d]
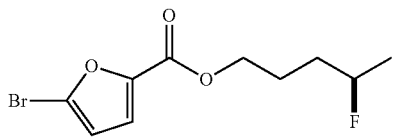
2l, 79%
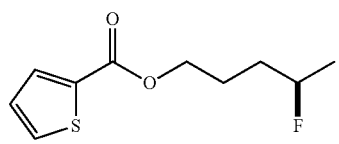
2m, 70%
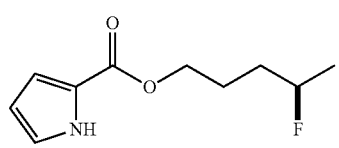
2n, 81%

TABLE 2-continued
Scope of Hydrofluorination of Alkenes.
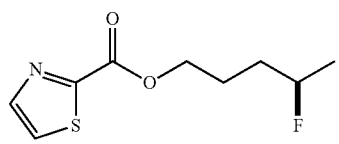
2o, 72%
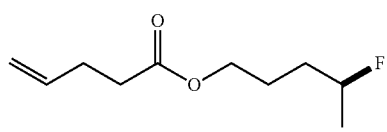
2p, 51%
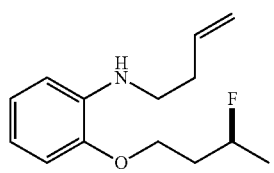 [SMILES: C=CCCNc1ccccc1OCC[C@H](C)F]
2q, 55%
b) Hydrofluorination of Disubstituted Alkenes
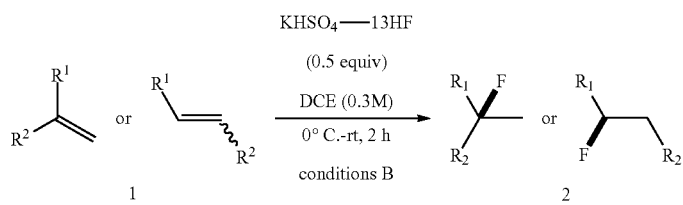
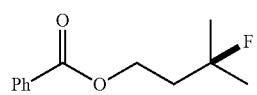
2r, 76%
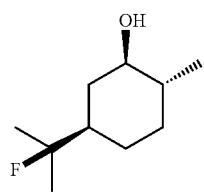
2s, 53%
Fluoro-(−)-Dihydrocarveol
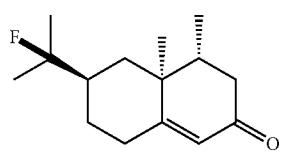
2t, 94%
Fluoro-(+)-Nootkatone TABLE 2-continued
Scope of Hydrofluorination of Alkenes.
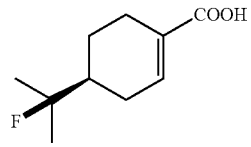
2u, 62%[e]
Fluoro-(S)-(−)-Perillic acid
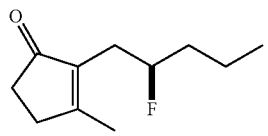
2v, 53%
(rr = 1.3:1)
Fluoro-cis-Jasmone
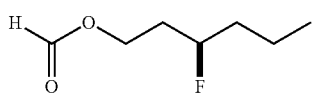
2w, 76%[f]
(rr = 2:1)
c) Hydrofluorination of Trisubstituted Alkenes
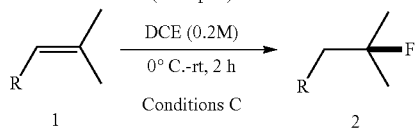
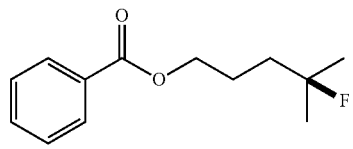
2x, 88%
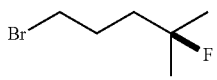
2y, 86%
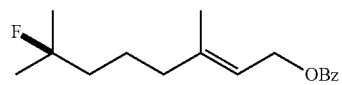
2z, 47%[g]
Fluoro-geranyl benzoate
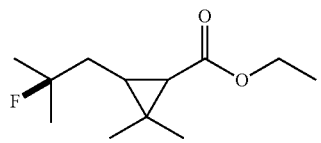
2aa, 61%
Fluoro-ethyl chrysanthemate

TABLE 2-continued

Scope of Hydrofluorination of Alkenes.

d) Chemoselectivity

Conditions A: alkene 1 (0.2 mmol), KHSO$_4$—13HF (1 equiv), DCE (0.2 mL), 0° C. to rt, 2 h.
Conditions B: alkene 1 (0.2 mmol), KHSO$_4$—13HF (0.5 equiv), DCE (0.6 mL), 0° C. to rt, 2 h.
Conditions C: alkene 1 (0.2 mmol), KHSO$_4$—13HF (0.5 equiv), DCE (1 mL), 0° C. to rt, 2 h.
[a]rt, 15 h;
[b]50° C., 2 h;
[c]rt, 15 h;
[d]2 equiv of KHSO$_4$—13HF was added;
[e]isomer ratio = 6:1;
[f]neat reaction, 30 mins, NMR yields.
[g]reverse addition: substrate solution was added to KHSO$_4$—13HF reagent.

In general, electron rich double bonds were more reactive (see 2t, 2u, 2v in Table 2). Dienes 1p, 1z and 1q, whose two double bonds are located in very similar environments, underwent hydrofluorination selectively (Table 2d and FIGS. 1-3). We calculated the HOMO of the starting alkenes and found that it correctly predicted the chemoselectivity in each case (FIGS. 1-3). The hydrofluorination occurred at the double bond bearing higher HOMO orbital density (Table 2d and FIGS. 1-3).

Our HF reagent was employed in a gram-scale hydrofluorination of (–)-β-citronellol. As shown below, 1.02 g of the fluorinated product 2ab was obtained (83% yield).

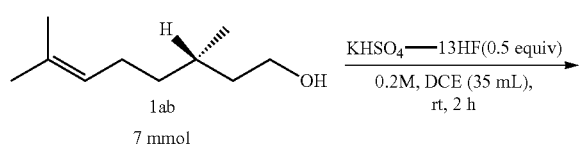

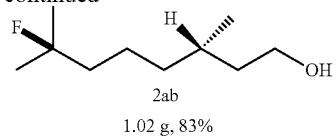

In summary, we have developed an HF reagent that, in some embodiments, is not only inexpensive and easily handled but is also efficient for the hydrofluorination of various functionalized alkenes. In other embodiments, the apparent functional group tolerance, Markovnikov addition regioselectivity, and atom economy can make this method an attractive protocol for the preparation of other fluorinated products.

The headings used in the disclosure are not meant to suggest that all disclosure relating to the heading is found within the section that starts with that heading. Disclosure for any subject may be found throughout the specification.

It is noted that terms like "preferably," "commonly," and "typically" are not used herein to limit the scope of the claimed invention or to imply that certain features are critical, essential, or even important to the structure or function of the claimed invention. Rather, these terms are merely intended to highlight alternative or additional features that may or may not be utilized in a particular embodiment of the present invention.

As used in the disclosure, "a" or "an" means one or more than one, unless otherwise specified. As used in the claims, when used in conjunction with the word "comprising" the words "a" or "an" means one or more than one, unless otherwise specified. As used in the disclosure or claims, "another" means at least a second or more, unless otherwise specified. As used in the disclosure, the phrases "such as", "for example", and "e.g." mean "for example, but not limited to" in that the list following the term ("such as", "for example", or "e.g.") provides some examples but the list is not necessarily a fully inclusive list. The word "comprising" means that the items following the word "comprising" may include additional unrecited elements or steps; that is, "comprising" does not exclude additional unrecited steps or elements.

Unless otherwise indicated, all numbers expressing quantities of ingredients, properties such as reaction conditions, and so forth used in the specification and claims are to be understood as being modified in all instances by the term "about". Accordingly, unless indicated to the contrary, the numerical parameters set forth in this specification and claims are approximations that can vary depending upon the desired properties sought to be obtained by the presently-disclosed subject matter.

As used herein, the term "about," when referring to a value or to an amount of mass, weight, time, volume, concentration or percentage is meant to encompass variations of in some embodiments ±20%, in some embodiments ±10%, in some embodiments ±5%, in some embodiments ±1%, in some embodiments ±0.5%, and in some embodiments ±0.1% from the specified amount, as such variations are appropriate to perform the disclosed method.

Detailed descriptions of one or more embodiments are provided herein. It is to be understood, however, that the present invention may be embodied in various forms. Therefore, specific details disclosed herein (even if designated as preferred or advantageous) are not to be interpreted as limiting, but rather are to be used as an illustrative basis for the claims and as a representative basis for teaching one skilled in the art to employ the present invention in any appropriate manner. Indeed, various modifications of the invention in addition to those described herein will become apparent to those skilled in the art from the foregoing description and the accompanying figures. Such modifications are intended to fall within the scope of the appended claims.

What is claimed is:

1. A catalyst selected from
   (a) Formula (Ia)
      $MHSO_4\text{-}xHF$ (Ia),
   (b) Formula (Ib)
      $M_2SO_4\text{-}xHF$ (Ib), and
   (c) Formula (Ic)
      $M^aSO_4\text{-}xHF$ (Ic);
   wherein
   M is $Li^+$, $Na^+$, $K^+$, $Rb^+$, $Cs^+$, or $NH_4^+$,
   $M^a$ is $Be^{2+}$, $Mg^{2+}$, $Ca^{2+}$, $Sr^{2+}$, $Ba^{2+}$, $Fe^{2+}$, $Zn^{2+}$, $Mn^{2+}$, $Ni^{2+}$, $Co^{2+}$, or $Cu^{2+}$, and
   x is 1, 2, 3, 4, 5, 6, 7, 8, 9, 10, 11, 12, 13, 14, 15, or 16.

2. The catalyst of claim 1, wherein the compound is selected from Formula (Ia).

3. The catalyst of claim 1, wherein x is 8, 9, 10, 11, 12, 13, 14, 15, or 16.

4. The catalyst of claim 1, wherein M is $Na^+$, $K^+$, or $NH_4^+$.

5. The catalyst of claim 1, wherein M is $K^+$.

6. The catalyst of claim 1, wherein the catalyst is $KHSO_4$-13HF.

7. A composition comprising the catalyst of claim 1 and a solvent.

8. The composition of claim 7, where the solvent is DCM (dichloromethane), DCE (1,2 dichloroethane), dioxane, $Et_2O$ (diethylether), $CH_3CN$, EtOAc (ethyl acetate), DMSO (dimethyl sulfoxide), DMF (dimethyl formamide), or toluene.

9. The composition of claim 7, where the solvent is DCM, DCE, or toluene.

10. A method for hydrofluorination of an organic compound comprising one or more alkenes, the method comprising contacting the organic compound comprising one or more alkenes with a catalyst of claim 1, wherein the contacting is optionally in the presence of a solvent.

11. The method of claim 10, wherein the contacting is in the presence of the solvent.

12. The method of claim 10, the method comprising
    (a) providing a mixture of the solvent and the organic compound comprising one or more alkenes; and
    (b) contacting the composition of (a) with the catalyst of claim 1, wherein the product molecule comprises one F on one of the carbons where an alkene was in the organic compound comprising one or more alkenes.

13. The method of claim 10, wherein x is 13.

14. The method of claim 10, wherein the catalyst is $KHSO_4$-13HF.

15. The method of claim 10, wherein the solvent is DCE.

16. The method of claim 10, wherein the amount of the organic molecule with at least one alkene is at least about 0.01 mmol.

17. The method of claim 10, wherein the contacting occurs for at least about 0.01 hours.

18. The method of claim 10, wherein the contacting occurs for from about 0.5 hours to about 2 hours.

19. The method of claim 10, wherein the temperature during the contacting is at least about −10° C.

20. The method of claim 10, wherein the organic compound comprising one or more alkenes is an organic compound comprising a monosubstituted alkene, a disubstituted alkene, or a trisubstituted alkene.

21. The method of claim 10, wherein the addition of the F is exclusive Markovnikov addition regioselectivity.

22. The method of claim 10, wherein the molecular weight of the organic compound comprising one or more alkenes is no more than about 3,000 daltons.

23. A method for preparing the catalyst of claim 1 comprising contacting HF with $MHSO_4$, $M_2SO_4$, or $M^aSO_4$.

24. The method of claim 23, wherein the contacting is at a temperature of no more than about 20° C.

25. The method of claim 23, wherein the mole ratio of HF to $MHSO_4$, $M_2SO_4$, or $M^aSO_4$ is at least about 5.

* * * * *